(12) United States Patent
Bell et al.

(10) Patent No.: US 11,963,829 B2
(45) Date of Patent: Apr. 23, 2024

(54) FIDUCIAL MARKERS FOR ANALYZING HUMAN JAWS

(71) Applicants: Patrick C. Bell, La Crosse, WI (US); Leo J. Malin, La Crosse, WI (US); Thomas J. Arendt, Norwalk, WI (US)

(72) Inventors: Patrick C. Bell, La Crosse, WI (US); Leo J. Malin, La Crosse, WI (US); Thomas J. Arendt, Norwalk, WI (US)

( * ) Notice: Subject to any disclaimer, the term of this patent is extended or adjusted under 35 U.S.C. 154(b) by 854 days.

(21) Appl. No.: 17/068,714

(22) Filed: Oct. 12, 2020

(65) Prior Publication Data

US 2021/0244516 A1 Aug. 12, 2021

Related U.S. Application Data

(63) Continuation-in-part of application No. 16/783,678, filed on Feb. 6, 2020, now Pat. No. 11,612,451.
(Continued)

(51) Int. Cl.
*A61B 90/00* (2016.01)
*A61B 5/055* (2006.01)
(Continued)

(52) U.S. Cl.
CPC ............ *A61B 90/39* (2016.02); *A61C 9/0046* (2013.01); *A61C 13/0004* (2013.01);
(Continued)

(58) Field of Classification Search
CPC ............ A61B 90/39; A61B 2090/3912; A61B 2090/3916; A61B 2090/3991; A61B 2090/3904; A61B 5/055; A61B 6/032; A61B 6/14; A61B 6/4085; A61B 6/4064; A61B 6/03; A61B 6/02; A61B 6/40; G06V 20/20; G06V 10/24; G06V 10/22;
(Continued)

(56) References Cited

U.S. PATENT DOCUMENTS 5,415,546 A 5/1995 Cox, Sr.
6,073,044 A 6/2000 Fitzpatrick et al.
(Continued)

FOREIGN PATENT DOCUMENTS

EP 1599148 B1 4/2011
KR 101594497 B1 2/2016
(Continued)

OTHER PUBLICATIONS

Wikipedia, definition of Polytetrafluoroethylene, (https://en.wikipedia.org/wiki/Polytetrafluoroethylene ) 2023.*
(Continued)

*Primary Examiner* — Ralph A Lewis
*Assistant Examiner* — Mirayda A Aponte
(74) *Attorney, Agent, or Firm* — bobharter.com; Robert J. Harter

(57) ABSTRACT

Example fiducial markers include features that make them particularly useful in dental scanning methods for analyzing jaws of a patient, wherein the dental scanning methods involve taking multiple scans of the jaws, and/or models thereof, and then shifting the image of one scan to match that of another. Prior to scanning, the fiducial markers are attached to the patient's jaws to accurately identify and track the relative position of the jaws.

10 Claims, 27 Drawing Sheets

Related U.S. Application Data

(60) Provisional application No. 62/978,778, filed on Feb. 19, 2020.

(51) Int. Cl.

| | | |
|---|---|---|
| *A61B 6/03* | (2006.01) | |
| *A61B 6/40* | (2024.01) | |
| *A61B 6/51* | (2024.01) | |
| *A61C 9/00* | (2006.01) | |
| *A61C 13/00* | (2006.01) | |
| *G06V 10/22* | (2022.01) | |
| *G06V 10/24* | (2022.01) | |
| *G06V 20/20* | (2022.01) | |

(52) U.S. Cl.
CPC .............. *G06V 10/22* (2022.01); *G06V 10/24* (2022.01); *G06V 20/20* (2022.01); *A61B 5/055* (2013.01); *A61B 6/032* (2013.01); *A61B 6/4085* (2013.01); *A61B 6/51* (2024.01); *A61B 2090/3912* (2016.02); *A61B 2090/3916* (2016.02); *A61B 2090/3991* (2016.02); *G06V 10/245* (2022.01); *G06V 2201/033* (2022.01)

(58) Field of Classification Search
CPC ................. G06V 10/245; G06V 10/20; G06V 2201/033; G06V 2201/00; A61C 9/0046; A61C 9/004; A61C 13/0004
USPC .......................................................... 433/29
See application file for complete search history.

(56) References Cited

U.S. PATENT DOCUMENTS

| | | | |
|---|---|---|---|
| 6,096,048 | A | 8/2000 | Howard, III et al. |
| 6,102,914 | A | 8/2000 | Bulstra et al. |
| 6,333,971 | B2 | 12/2001 | McCrory et al. |
| 6,499,488 | B1 | 12/2002 | Hunter et al. |
| 6,565,573 | B1 | 5/2003 | Ferrante et al. |
| 6,582,931 | B1 | 6/2003 | Kois et al. |
| 6,866,666 | B1 | 3/2005 | Sinnott et al. |
| 6,942,667 | B1 | 9/2005 | Song |
| D528,211 | S | 9/2006 | Solar et al. |
| 7,601,000 | B1 | 10/2009 | Hammond |
| 7,787,934 | B2 | 8/2010 | Mazzocchi et al. |
| 8,170,645 | B2 | 5/2012 | Solar et al. |
| 8,172,573 | B2 | 5/2012 | Sonenfeld et al. |
| 8,185,184 | B2 | 5/2012 | Solar et al. |
| 8,808,000 | B2 | 8/2014 | Salcedo et al. |
| 9,265,590 | B2 | 2/2016 | Zagorchev et al. |
| 9,554,869 | B1 | 1/2017 | Huang et al. |
| 9,877,810 | B2 | 1/2018 | Mozes et al. |
| 9,955,929 | B2 | 5/2018 | Huang et al. |
| 10,022,104 | B2 | 7/2018 | Sell et al. |
| 10,952,814 | B2 | 3/2021 | Kim et al. |
| 2001/0004395 | A1 | 6/2001 | McCrory et al. |
| 2002/0094509 | A1 | 7/2002 | Durbin |
| 2004/0030236 | A1 | 2/2004 | Mazzocchi et al. |
| 2004/0030237 | A1 | 2/2004 | Lee et al. |
| 2004/0167393 | A1 | 8/2004 | Solar et al. |
| 2006/0121409 | A1 | 6/2006 | Olivier |
| 2006/0241406 | A1 | 10/2006 | Noujeim |
| 2008/0234532 | A1 | 9/2008 | De Langen et al. |
| 2013/0172731 | A1* | 7/2013 | Gole ...................... A61B 6/506 600/424 |
| 2013/0337400 | A1 | 12/2013 | Yi et al. |
| 2014/0270067 | A1 | 9/2014 | Clark |
| 2014/0379356 | A1 | 12/2014 | Sachdeva |
| 2015/0030993 | A1* | 1/2015 | von Malottki ....... A61C 8/0066 433/173 |
| 2018/0333231 | A1 | 11/2018 | Somasundaram et al. |
| 2019/0151046 | A1 | 5/2019 | Kim et al. |

FOREIGN PATENT DOCUMENTS

| | | | |
|---|---|---|---|
| WO | WO2007019113 A2 | 2/2007 | |
| WO | WO-2017070358 A1 * | 4/2017 | ......... A61C 13/0004 |
| WO | WO 2019151923 A1 | 8/2019 | |

OTHER PUBLICATIONS

Wikipedia, definition of Stainless Steel, (https://en.wikipedia.org/wiki/Stainless_steel) 2023.*
TAB2, Summary of Safety and Effectiveness, 510(k) Summary per 21 CFR 807.92(c), Self-Drilling Radiographic Marker, Jacksonville, Florida, 4 pages, published May 13, 2004.
Unitek, TAD Temporaty Anchorage Device, 3M Company, St. Paul, MN; www.3m.com/3M/en_US/company-us/all-3m-products/~/Unitek-TADs/?N=5002385+3290412411&preselect=8710666&rt=rud; website; one page plus hyperlinks to related information; publically available and retrieved for viewing on Feb. 4, 2020.
Dentsply, Dentsply Sirona Company, Salzburg, Austria; www.dentsplysirona.com; website; 2 pages plus hyperlinks to various dental tools and software, publically available and retrieved for viewing on Feb. 4, 2020.
Dental Wings, Welcome to Dental Wings, Straumann Group Dental Wings Company, Montreal, Quebec, www.dentalwings.com; website; 2 pages plus hyperlinks to various dental software downloads, publically available and retrieved for viewing on Feb. 4, 2020.
3Shape, We Innovate for Superior Patient Care, 3Shape Company, CopenHagen, Denmark, www.3shape.com website, 2 pages plus hyperlinks, publically available and retrieved for viewing on Feb. 4, 2020.
Exocad, Your Future in Digital Dentistry, exocad GmbH Company, Darmstadt, Hessen, www.exocad.com website, 2 pages plus hyperlinks, publically available and retrieved for viewing on Feb. 4, 2020.
Sha; Medical Device and Diagnostic Industry; Radiopaque Polymer Formulations for Medical Devices; Tilak M. Shah; Los Angeles, CA; 6 pages; Mar. 2000.
Gold Dust; How to Take a Stick Bite Your Lab can Use; Gold Dust Dental Lab; Tempe, AZ; 1 page, Nov. 12, 2015.
Scherer, Michael D.; Presurgical Implant-Site Assessment and Restoratively Driven Digital Planning; Dental Clinics of North America, vol. 58, Issue 3; 35 pages (pp. 561-595); dated Jul. 2014.
International Search Report, issued in connection with PCT/US2021/016917, dated Mar. 29, 2021, 8 pages.
International Search Report, issued in connection with PCT/US2021/012871, dated Mar. 25, 2021, 10 pages.
International Search Report, issued in connection with PCT/US2021/012791, dated Mar. 26, 2021, 10 pages.

* cited by examiner

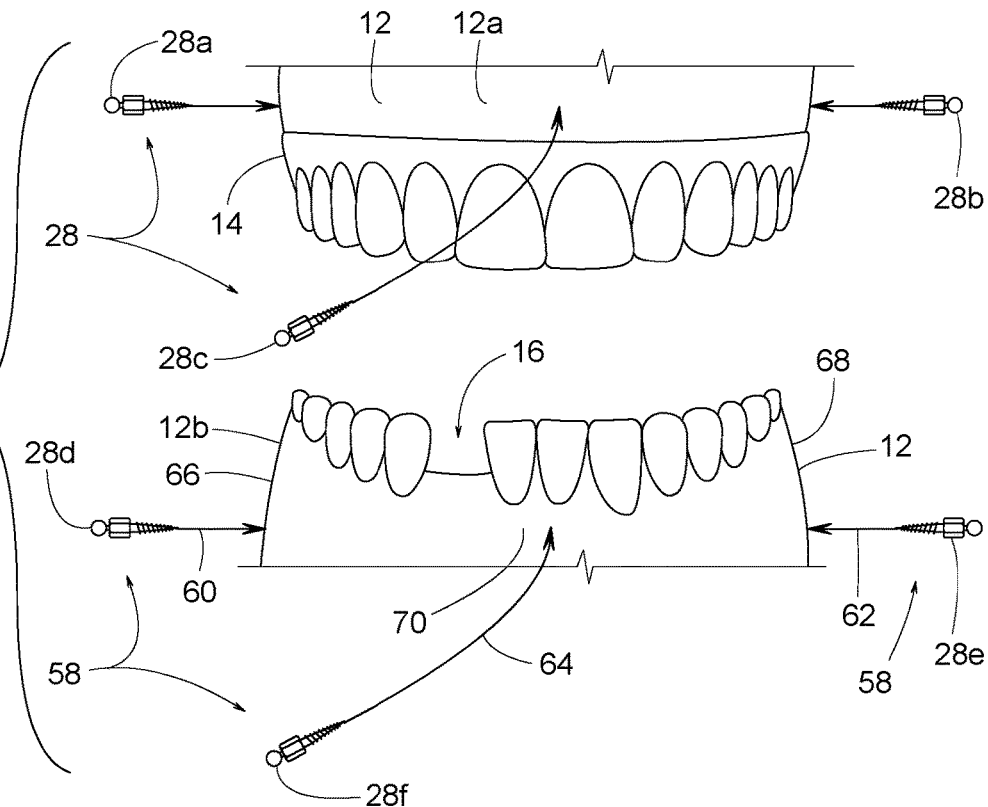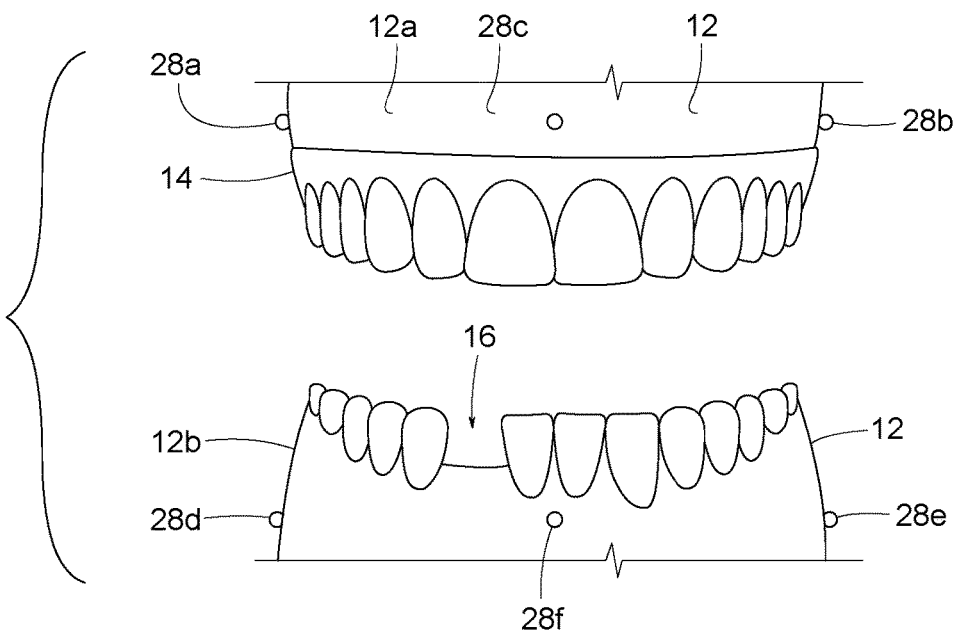

--- making a size comparison, via the computer executing digital image analytics, of the second scanned representation of the first jaw relative to the first scanned representation of the first jaw iteratively adjusting, via the computer executing digital image analytics, a scale of at least one of the first scanned representation of the first jaw and the second scanned representation of the first jaw relative until the first scanned representation of the first jaw and the second scanned representation of the first jaw substantially match in scale making an X-axis comparison, via the computer executing digital image analytics, of the second scanned representation of the first jaw and the first scanned representation of the first jaw with reference to the first scanned representation of the second jaw iteratively adjusting, via the computer executing digital image analytics, an X-axis position of the second scanned representation of the first jaw relative until the first second scanned representation of the first jaw and the first scanned representation of the first jaw substantially match with reference to an X-axis making a Y-axis comparison, via the computer executing digital image analytics, of the second scanned representation of the first jaw and the first scanned representation of the first jaw with reference to the first scanned representation of the second jaw iteratively adjusting, via the computer executing digital image analytics, a Y-axis position of the second scanned representation of the first jaw relative until the first second scanned representation of the first jaw and the first scanned representation of the first jaw substantially match with reference to a Y-axis making a Z-axis comparison, via the computer executing digital image analytics, of the second scanned representation of the first jaw and the first scanned representation of the first jaw with reference to the first scanned representation of the second jaw iteratively adjusting, via the computer executing digital image analytics, a Z-axis position of the second scanned representation of the first jaw relative until the first second scanned representation of the first jaw and the first scanned representation of the first jaw substantially match with reference to a Z-axis making a pitch comparison, via the computer executing digital image analytics, of the second scanned representation of the first jaw and the first scanned representation of the first jaw, the pitch comparison being with reference to rotation about the X-axis iteratively adjusting, via the computer executing digital image analytics, a pitch orientation of the second scanned representation of the first jaw relative until the second scanned representation of the first jaw and the first scanned representation of the first jaw substantially match with reference to a pitch about the X-axis making a roll comparison, via the computer executing digital image analytics, of the second scanned representation of the first jaw and the first scanned representation of the first jaw, the roll comparison being with reference to rotation about the Z-axis iteratively adjusting, via the computer executing digital image analytics, a roll orientation of the second scanned representation of the first jaw relative until the second scanned representation of the first jaw and the first scanned representation of the first jaw substantially match with reference to a roll about the Z-axis making a yaw comparison, via the computer executing digital image analytics, of the second scanned representation of the first jaw and the first scanned representation of the first jaw, the yaw comparison being with reference to rotation about the Z-axis iteratively adjusting, via the computer executing digital image analytics, a yaw orientation of the second scanned representation of the first jaw relative until the second scanned representation of the first jaw and the first scanned

FIDUCIAL MARKERS FOR ANALYZING HUMAN JAWS

CROSS REFERENCE TO RELATED APPLICATIONS

This application is a continuation-in-part of patent application Ser. No. 16/783,678 filed on Feb. 6, 2020 and claims the benefit of provisional patent application Ser. No. 62/978,778 filed on Feb. 19, 2020.

FIELD OF THE DISCLOSURE

This patent generally pertains to dentistry and more specifically to fiducial markers attachable to human jaws to assist a dental practitioner in comparing multiple radiographic scans of the jaws and attached markers to analyze bite registration and other jaw-related features.

BACKGROUND

A typical jaw of a person or human patient includes a maxilla (upper jaw) and a mandible (lower jaw). Temporamandibular joints (TMJ) allow pivotal and some translational relative movement between the maxilla and mandible, so the person can pivotally open and close their mouth. Both the maxilla and mandible comprise an alveolar bone for supporting teeth. A curved portion of the alveolar bone is known as the alveolar arch, which curves about an oral cavity within the person's mouth. The oral cavity is the space that contains the person's tongue.

Normally, when a person closes their mouth, the teeth in the upper and lower jaws come together in a comfortable engaging relationship known as proper bite registration. Other times, however, malpositioned teeth, missing teeth or interfering dental appliances prevent the jaws from closing in proper bite registration. This can create a number of problems such as stressing the temporamandibular joints, concentrating localized force on certain teeth, and creating a poor visual appearance. Consequently, various dental treatments are used for correcting such problems.

Planning and performing certain dental treatments might first involve creating physical cast models of a patient's upper and lower jaws and analyzing how well the cast models fit together before and after treatment. Some example treatments include installing dentures, repairing dentures, installing implants, applying crowns, jaw surgery, applying braces, and removing teeth.

In some cases, various scanners are used for assisting in the dental treatment process. Some scanners generate a dicom file, which is an acronym for Digital Imaging and Communications in Medicine. Some dicom files have a .dcm file extension.

BRIEF DESCRIPTION OF THE DRAWINGS

FIG. 6 is a front view similar to FIG. 4 but showing fiducial markers being installed in both the upper and lower jaws.

FIG. 7 is a front view similar to FIG. 6 but showing the fiducial markers already installed.

FIG. 37 is a flow chart illustrating example steps in digital image analytics for iteratively adjusting a digital image.

DETAILED DESCRIPTION

FIGS. 1-27 pertain to a dental scanning method for analyzing jaws of a patient 10 by taking multiple scans of the jaws, and/or models thereof, and then shifting the image of one scan to match that of another. In some examples, fiducial markers are attached to the patient's jaws beforehand to accurately identify and track the relative position of the jaws. The method provides a way for creating a precise image of an upper jaw 12a and a lower jaw 12b in their proper bite registration, even though the resulting image may show an insufficient number of teeth to readily do so. The final, properly shifted image serves as a virtual 3D jaw that can be manipulated and analyzed to aid in various orthodontic and other dental treatments.

Figure 1:
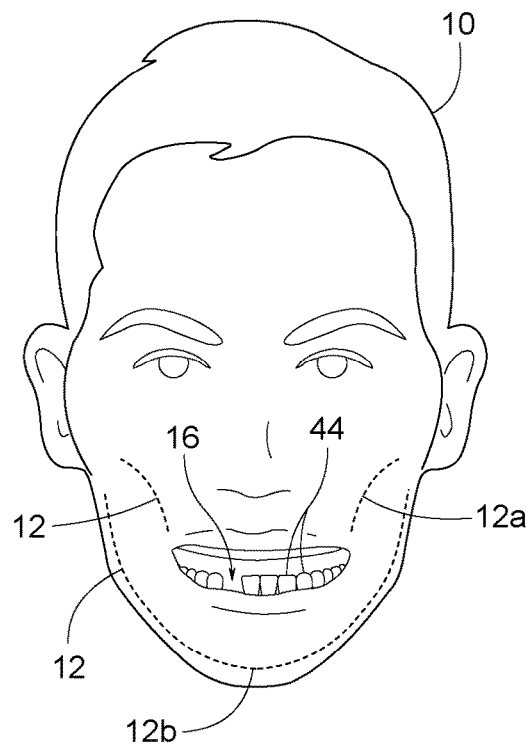
FIG. 1 is a front view of an example patient that has no upper teeth and is missing one lower tooth.
Figure 2:
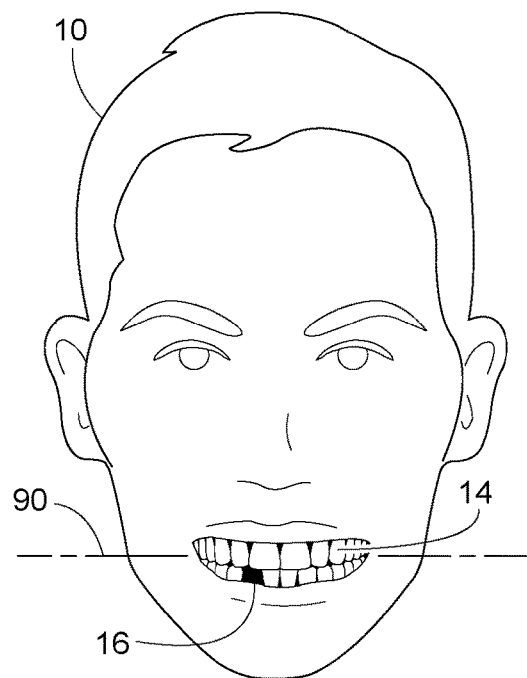
FIG. 2 is a front view of the patient shown in FIG. 1 but with the addition of a poor-fitting upper denture.

The method can be applied to an infinite variety of patients and treatments. Some example treatments include installing dentures, repairing dentures, installing implants, applying crowns, jaw surgery, grinding teeth, shifting teeth, removing teeth, and all other conceivable modifications to the craniofacial complex. For sake of example, the present method can be applied to patient 10, shown in FIGS. 1-3. In this particular example, patient 10 has no upper teeth and is missing a lower tooth, as shown in FIG. 1. Prior to using the method disclosed herein, patient 10 wore an old, poor fitting upper denture 14 and left an area 16 of the missing lower tooth open, as shown in FIG. 2.

Figure 3:
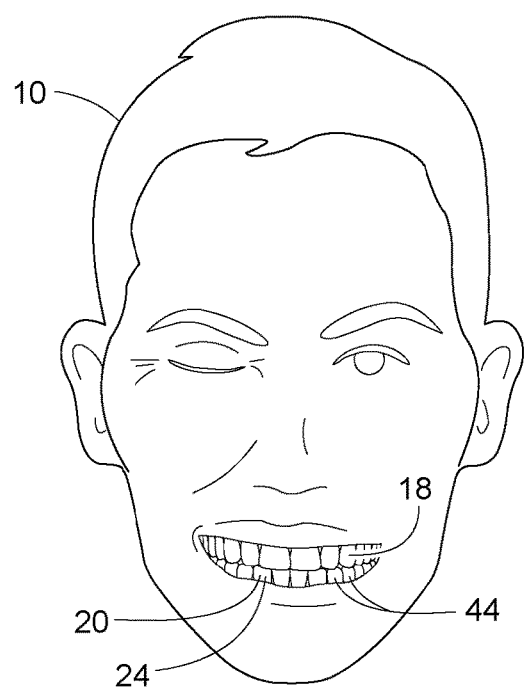
FIG. 3 is a front view of the patient shown in FIG. 1 but with the addition of a new upper denture and an implant replacing the missing lower tooth.

Following treatment, patient 10 is provided with a well fitting upper denture 18 plus an implant 20 to fill the space of the missing tooth, as shown in FIG. 3. The term, "implant" refers to an anchor 22 attached to a jaw bone and/or a crown 24 attached to anchor 22. Some example implants further include a post 26 (e.g., a screw, a rod, a pin, etc.) for fastening crown 24 to anchor 22.

Patient 10 has two jaw members 12 including upper jaw 12*a* (maxilla) and lower jaw 12*b* (mandible). The term, "first jaw" refers to either jaw, the maxilla or the mandible. Likewise, the term, "second jaw" refers interchangeably to the maxilla or mandible. FIGS. 4-7, 11 and 12 show the patient's actual jaw members 12, not models thereof. FIGS. 4-7 show jaws 12*a* and 12*b* in the condition similar to that shown in FIG. 2, wherein old denture 14 is on upper jaw 12*a* and space 16 is left empty.

To provide jaw 12*a* and/or jaw 12*b* with reference points that help identify the jaws' relative location and orientation in later scanned images of jaws 12*a* and 12*b*, some example methods involve installing multiple fiducial markers 28 into an alveolar bone 30 (FIGS. 8 and 9) of jaw 12*a* and/or 12*b*. The term, "alveolar bone" refers to the bony structure of either jaw 12*a* or 12*b*. The term, "fiducial marker" refers to any item that includes a substantially radiopaque feature.

Figure 25:
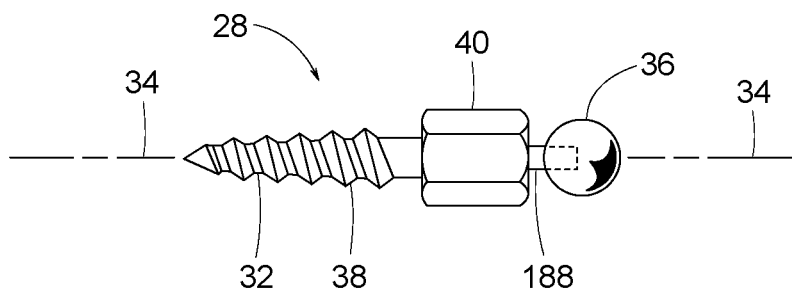
FIG. 25 is a side view of an example fiducial marker constructed in accordance with the teachings disclosed herein.
Figure 26:
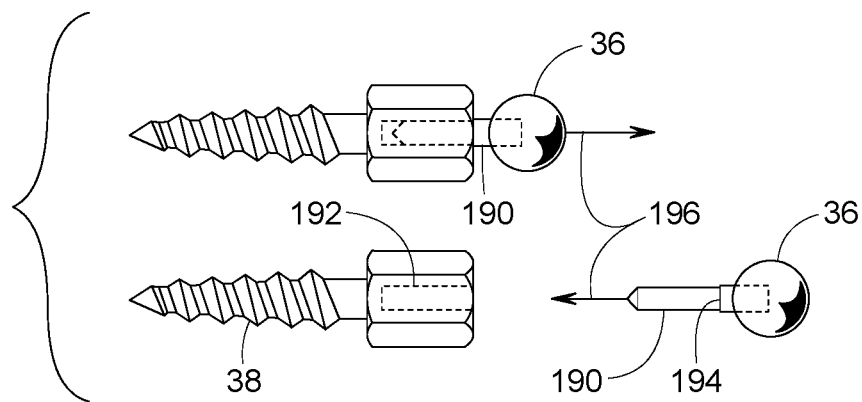
FIG. 26 are side views of another example fiducial marker constructed in accordance with the teachings disclosed herein.
Figure 27:
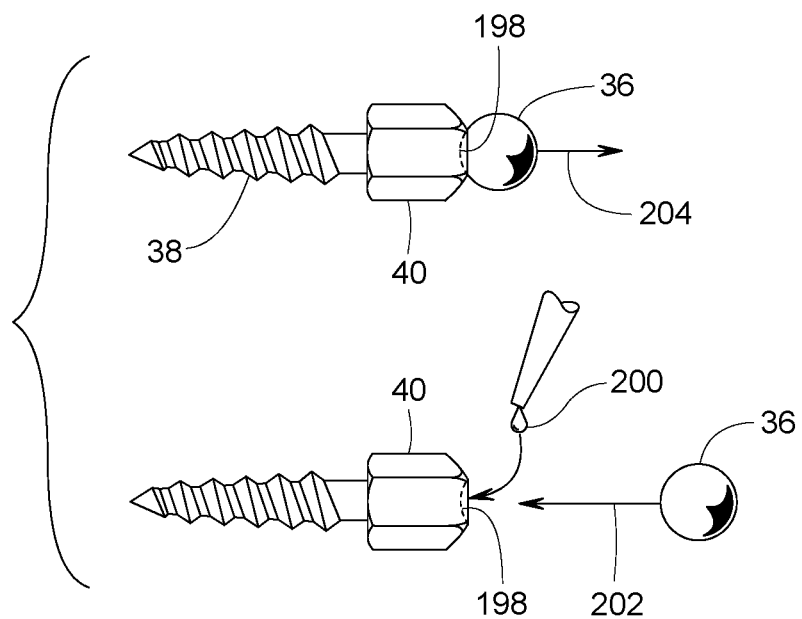
FIG. 27 are side views of yet another example fiducial marker constructed in accordance with the teachings disclosed herein.

Some examples of fiducial marker 28 comprise a shaft 32 extending along a longitudinal axis 34 from a marker body 36. The term, "shaft" refers to any elongate member that is generally cylindrical, tapered and/or threaded. Some examples of shaft 32 include a screw, a straight pin, a tapered pin, a rod, a nail, etc. In the illustrated examples, shaft 32 is a screw 38. The term, "marker body" refers to any structure of any shape that is substantially radiopaque. In some examples, marker body 36 is generally spherical and made of a polymer with 10% barium sulfate. In some examples, marker body 36 is overmolded or otherwise attached to a head 40 of screw 38. Some examples of screw 38 are made of a generally noncorrosive material, such as stainless steel, carbide or titanium. Head 40, in some examples, has a tool-mating geometry, so screw 38 can be readily driven into jaw member 12. Various examples of fiducial marker 28 are shown in FIGS. 25-27 and will be described later in more detail.

Figure 4:
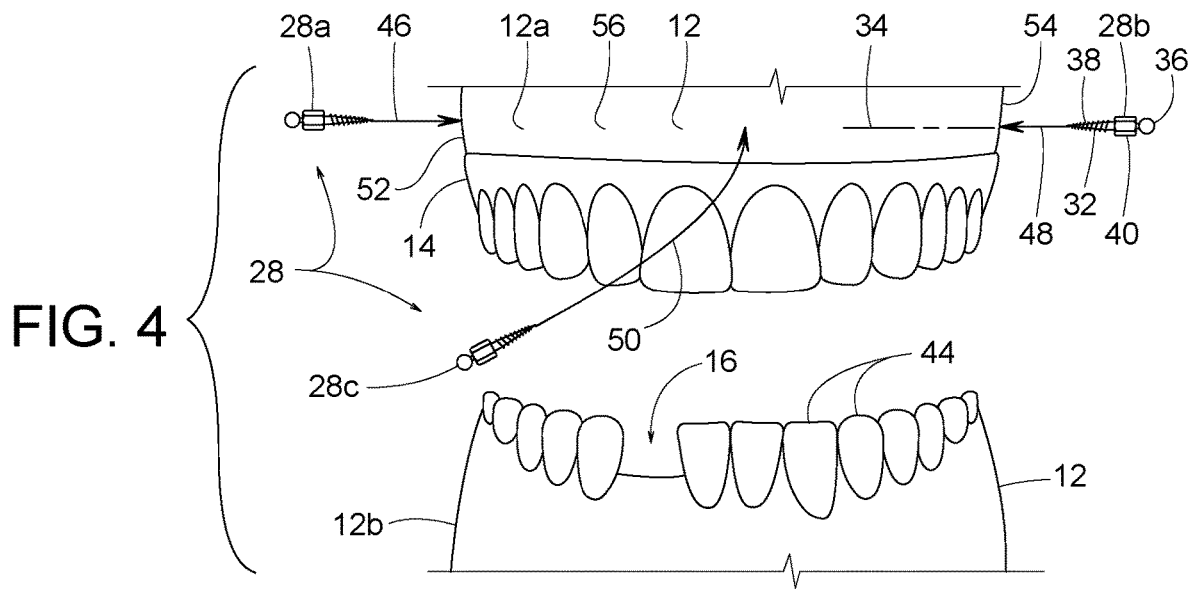
FIG. 4 is a front view of the patient's upper and lower jaws with fiducial markers being installed in the upper jaw, just above the poor-fitting upper denture.
Figure 5:
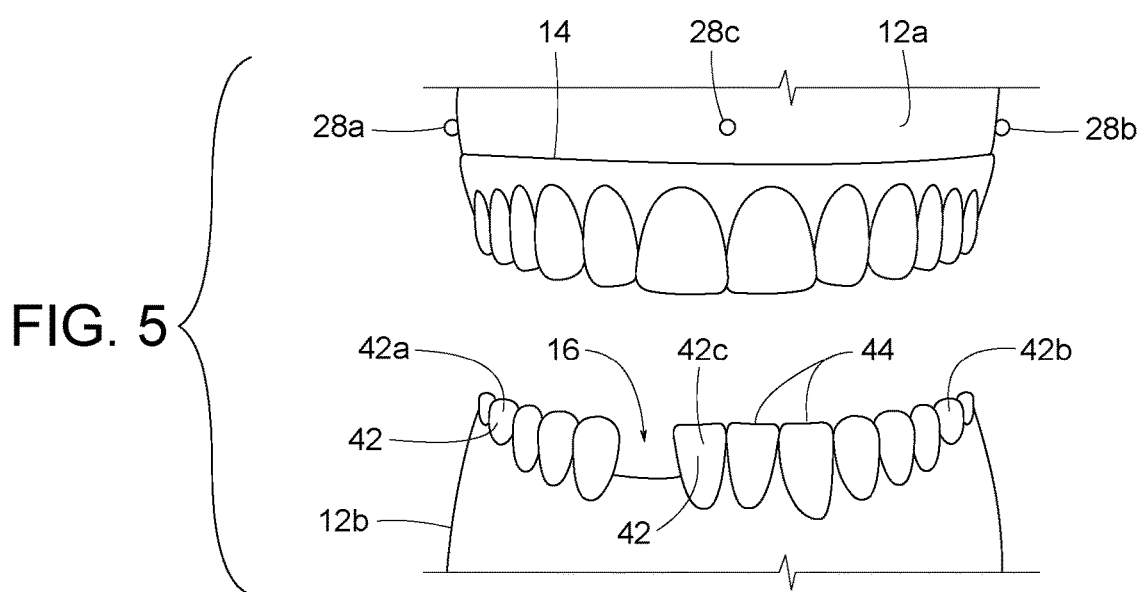
FIG. 5 is a front view similar to FIG. 4 but showing the fiducial markers already installed.

For minimal invasiveness, in some examples, markers 28 are only installed in one of jaw members 12, as shown in FIGS. 4 and 5, and distinct stable features 42 of teeth 44 are used as reference points on the other jaw member 12. Some examples of features 42 include chosen edges, corners, faces, and peaks of individual teeth 44 or a dental appliance supported by one of the jaws 12. More specific examples include a first feature 42*a* (face of a first chosen tooth), a second feature 42*b* (face of a second chosen tooth), and a third feature 42*c* (face of a third chosen tooth).

In the example shown in FIGS. 4 and 5, fiducial markers 28 include a right fiducial marker 28*a*, a left fiducial marker 28*b*, and a front fiducial marker 28*c*. Arrows 46, 48 and 50 respectively represent attaching right fiducial marker 28*a* to a right portion 52 of first jaw 12*a*, attaching left fiducial marker 28*b* to a left portion 54 of first jaw 12*a*, and attaching front fiducial marker 28*c* to a front portion 56 of first jaw 12*a*. FIG. 5 shows markers 28*a*, 28*b* and 28*c* in their installed positions. Such a spread-out arrangement of three markers 28 provides upper jaw 12*a* with a broad footprint for maximum positional accuracy.

In addition or alternatively, FIGS. 6 and 7 show the installation of a second set 58 of three fiducial markers 28 comprising a right fiducial marker 28*d*, a left fiducial marker 28*e*, and a front fiducial marker 28*f*. Arrows 60, 62 and 64 respectively represent attaching left fiducial marker 28*d* to a right portion 66 of second jaw 12*b*, attaching left fiducial marker 28*e* to a left portion 68 of second jaw 12*b*, and attaching front fiducial marker 28*f* to a front portion 70 of second jaw 12*b*. FIG. 6 shows markers 28*d*, 28*e* and 28*f* in their installed positions.

In some examples, the second set 58 of fiducial markers 28 provides a more precise indication of the second jaw's location and orientation than what is otherwise achieved by relying instead on distinct features 42 of teeth 44. This is because markers 28*d*, 28*e*, and 28*f* can be more spread out than teeth 44, and the size of marker bodies 36 is usually smaller than teeth 44.

Figure 8:
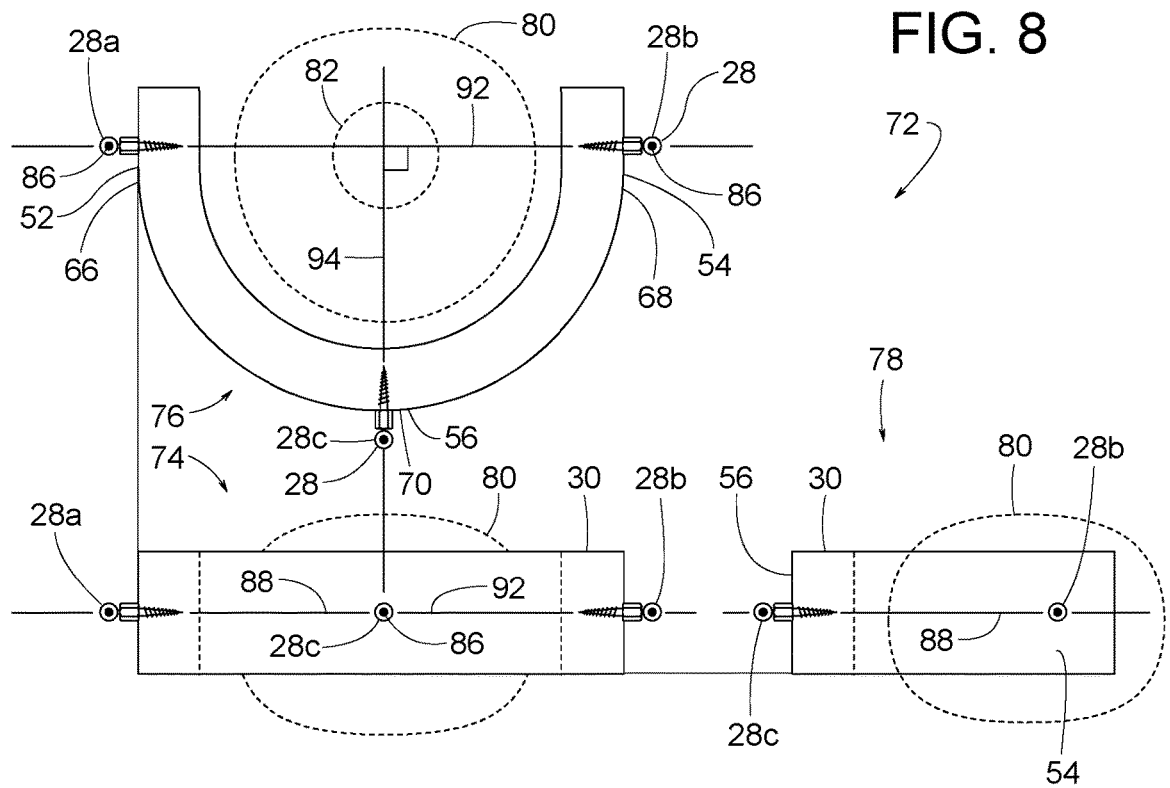
FIG. 8 is a set of orthogonal views showing an example scanning arrangement of fiducial markers screwed into in a schematically illustrated alveolar bone of either an upper or lower jaw.
Figure 9:
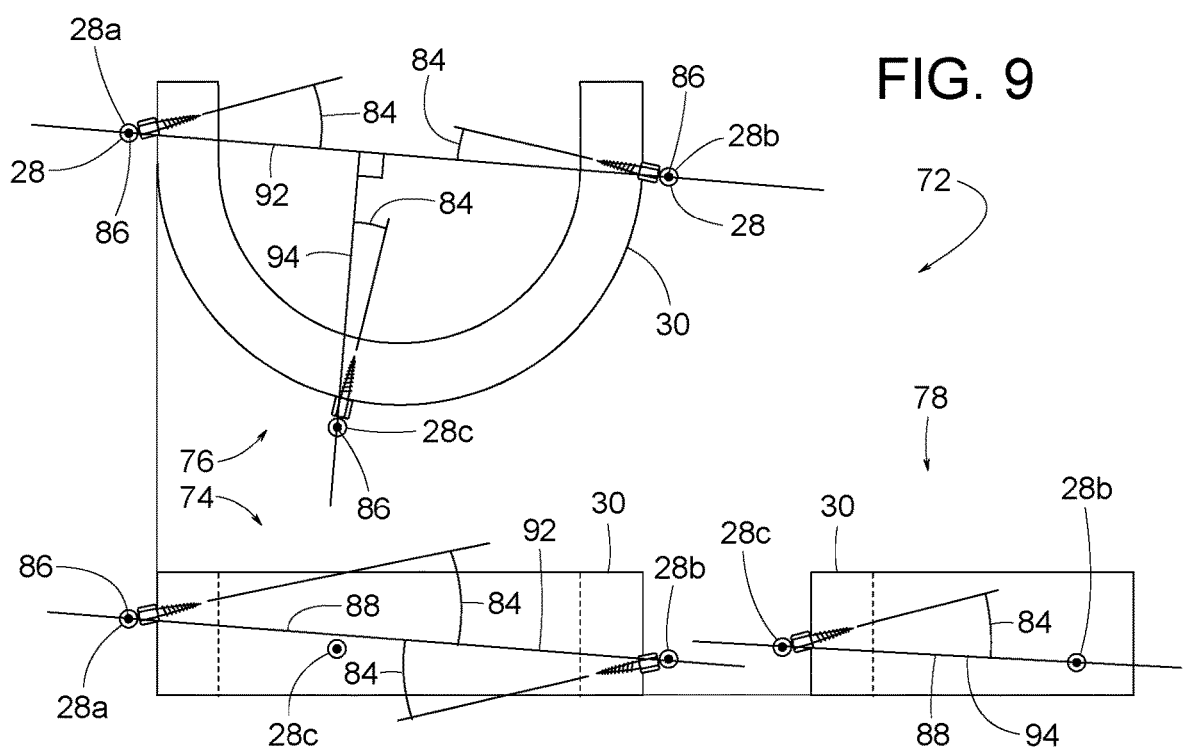
FIG. 9 is a set of orthogonal views showing another example scanning arrangement of fiducial markers screwed into in a schematically illustrated alveolar bone of either an upper or lower jaw.

FIGS. 8 and 9 are sets of orthogonal views showing example scanning arrangements 72 of fiducial markers 28 screwed into in a schematically illustrated alveolar bone 30 of either jaw member 12. FIG. 8 shows a front view 74, a top view 76, and a right side view 78 of jaw member 12 with fiducial markers 28 in an ideal arrangement. FIG. 9 shows the same views 74, 76 and 78 but with fiducial markers 28 in a more misaligned yet still acceptable configuration. From a vertical perspective, as shown in top view 76 of FIGS. 8 and 9, fiducial markers 28 extend beyond the general outer perimeter of jaw member 12 (i.e., outer perimeter in the vicinity of markers 28). Fiducial markers 28 thus provide a broader footprint for greater positional accuracy, as mentioned earlier.

FIGS. 8 and 9 show fiducial markers 28 and alveolar bone 30 in relation to an oral cavity 80 of patient 10. Oral cavity 80 is the area surrounded by alveolar bone 30. In the illustrated examples, screw 38 of each of the three fiducial markers 28 points inward toward a central region 82 of oral cavity 80 when fiducial markers 28 are attached to alveolar bone 30.

In some examples, for maxilla 12*a*, fiducial marker 28*c* is installed just below the midline of the anterior nasal spine, at the end of the superior labial frenulum. In some examples, fiducial markers 28*a* and 28*b* are installed just anterior of the maxillary tuberosity, with marker 28*a* on the right side and marker 28*b* on the left side.

In some examples, for mandible 12*b*, fiducial marker 28*f* is installed in the medial border of the hemi-mandible, near the alveolar crest. In some examples, fiducial markers 28*d* and 28*e* are installed along the oblique line, just below the posterior-most teeth, with marker 28*d* on the right side and marker 28*e* on the left side.

It has been discovered that the arrangements shown in FIGS. 8 and 9 provide good results when each fiducial marker's angular deviation (angle 84) is within 45 degrees of a predetermined ideal layout. More specifically, in the illustrated examples, each marker body 28 defines a center point 86 and are arranged such that:

a) center points 86 of fiducial markers 28*a*, 28*b* and 28*c* define a plane 88 (in some examples, plane 88 is generally parallel to an occlusal plane 90 of patient 10);

b) center point 86 of left fiducial marker 28*b* and center point 86 of right fiducial marker 28*a* define a lateral line 92 intersecting center point 86 of left fiducial marker 28*b* and center point 86 of right fiducial marker 28*a*;

c) center point 86 of front fiducial marker 28*c* defines a forward line 94 intersecting center point 86 of front fiducial marker 28*c*, intersecting lateral line 92, and being perpendicular to lateral line 92;

d) shaft 32 of left fiducial marker 28*b* lies within an angle 84 of 45 degrees of lateral line 92 as viewed from a direction perpendicular to plane 88;

e) shaft 32 of left fiducial marker 28*b* lies within an angle 84 of 45 degrees of lateral line 92 as viewed from a direction parallel to plane 88 and perpendicular to lateral line 92;

f) shaft 32 of right fiducial marker 28*a* lies within an angle 84 of 45 degrees of lateral line 92;

g) shaft 32 of right fiducial marker 28*a* lies within an angle 84 of 45 degrees of lateral line 92 as viewed from a direction parallel to plane 88 and perpendicular to lateral line 92;

h) shaft 32 of front fiducial marker 28*c* lies within an angle 84 of 45 degrees of forward line 94; and i) shaft 32 of front fiducial marker 28*c* lies within an angle 84 of 45 degrees of lateral line 92 as viewed from a direction parallel to plane 88 and perpendicular to lateral line 92.

Figure 10:
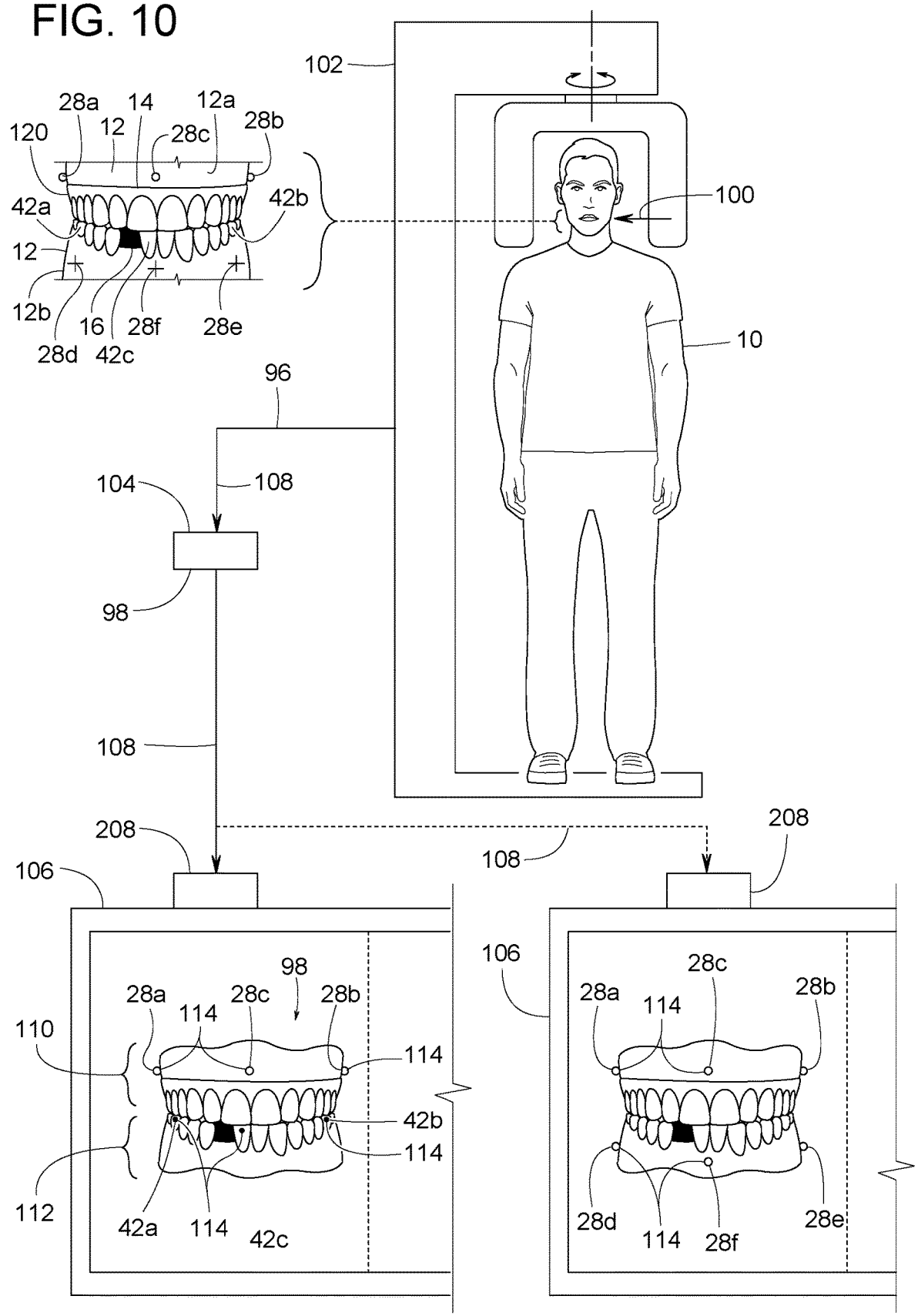
FIG. 10 is a schematic diagram illustrating various method steps associated with a first scanning machine.

In the example shown in FIGS. 4, 5 and 10, three fiducial markers 28*a*, 28*b* and 28*c* in upper jaw 12*a* and three features 42*a*, 42*b* and 42*c* of lower jaw 12*b* will be used as clear, distinct reference points for marking the location of upper jaw 12*a* relative to lower jaw 12*b*. Further steps in some examples of the present dental scanning method will now be explained with reference to FIGS. 10-24.

FIG. 10 illustrates creating 96 a first scan result 98 by scanning 100 first jaw 12*a*, second jaw 12*b*; three fiducial markers 28*a*, 28*b* and 28*c* on first jaw 12*a*; and three features 42*a*, 42*b* and 42*c* on second jaw 12*b*. In some examples, first scan result 98 is created by scanning 100 fiducial markers 28*d*, 28*e* and 28*f* in addition or alternatively to capturing features 42*a*, 42*b* and 42*c*.

In either case, scanning 100 is done while jaws 12 are in a predetermined target bite position relative to each other. In some examples, the predetermined target bite position is referred to as a proper bite registration, wherein the teeth and/or other installed dental appliances fit comfortably together in a generally closed position without subjecting the temporamandibular joints to undo stress. An example of such a predetermined target bite position, or proper bite registration, is shown in FIG. 2 and the upper left corner of FIG. 10.

The term, "dental appliance" refers to any device temporarily or permanently installed within a patient's mouth. Some example dental appliances include full dentures, partial dentures, bridges, crowns, cavity fillings, braces, implants, etc. In some examples, dental appliances and a patient's actual teeth are some examples of "spacers," as both teeth and dental appliances limit how closely upper jaw 12*a* and lower jaw 12*b* can come together.

Scanning 100, as shown in FIG. 10, can be done by any suitable scanning method. Some example methods of scanning 100 include cone beam computed tomography (CBCT), magnetic resonance imaging (MRI), computed tomography (CT or CAT), X-ray, etc. In some examples, scanning 100 is performed using a CBCT scanning machine 102 (first scanning machine 102). Some examples of first scanning machine 102 include an i-Cat FLX.I cone beam 3D imaging scanner manufactured by Imaging Sciences International LLC of Alpharetta, Georgia or Hatfield, Pennsylvania.

From first scanning machine 102, first scan result 98 is transferred in a file format 104 to a computer 106, as indicated by arrows 108 of FIG. 10. In some examples, first scanning machine 102 generates first scan result 98 in a first format (e.g., a dicom file), and computer 106 converts the first format to a more manageable digital format (e.g., an stl file). In some examples, the file conversion is accomplished through dental treatment planning software executed by computer 106. Some examples of such software include exocad, 3shape, dental wings, and Dentsply Sirona. In other examples, first scanning machine 102 generates first scan result 98 directly in a more manageable digital format without the need for subsequent file conversion by computer 106.

FIG. 10 also shows computer 106 displaying first scan result 98 including a first scanned representation of the first jaw 110, a first scanned representation of the second jaw 112, and a first constellation of points 114. In some examples, first constellation of points 114 represents three fiducial markers 28*a*, 28*b* and 28*c*; as shown in the left-bottom of FIG. 10. In some examples, first constellation of points 114 represents three fiducial markers 28*a*, 28*b* and 28*c* on first jaw 12*a* plus three features 42*a*, 42*b* and 42*c* on second jaw 12*b*; also shown in the left-bottom of FIG. 10. In some examples, first constellation of points 114 represents three fiducial markers 28*a*, 28*b* and 28*c* on first jaw 12*a* plus second set 58 of three fiducial markers 28*d*, 28*e* and 28*f* on second jaw 12*b*; shown in the right-bottom of FIG. 10.

First scan result 98, regardless of which example of first constellation of points 114 is being used, provides a reference against which subsequent scans will be compared. Such later scans will be used for creating an accurate digital jaw model 116 (FIGS. 20, 23 and 24) that can be manipulated and analyzed in the treatment of patient 10. Various method steps for producing such scans are shown in FIGS. 11-14.

Figure 11:
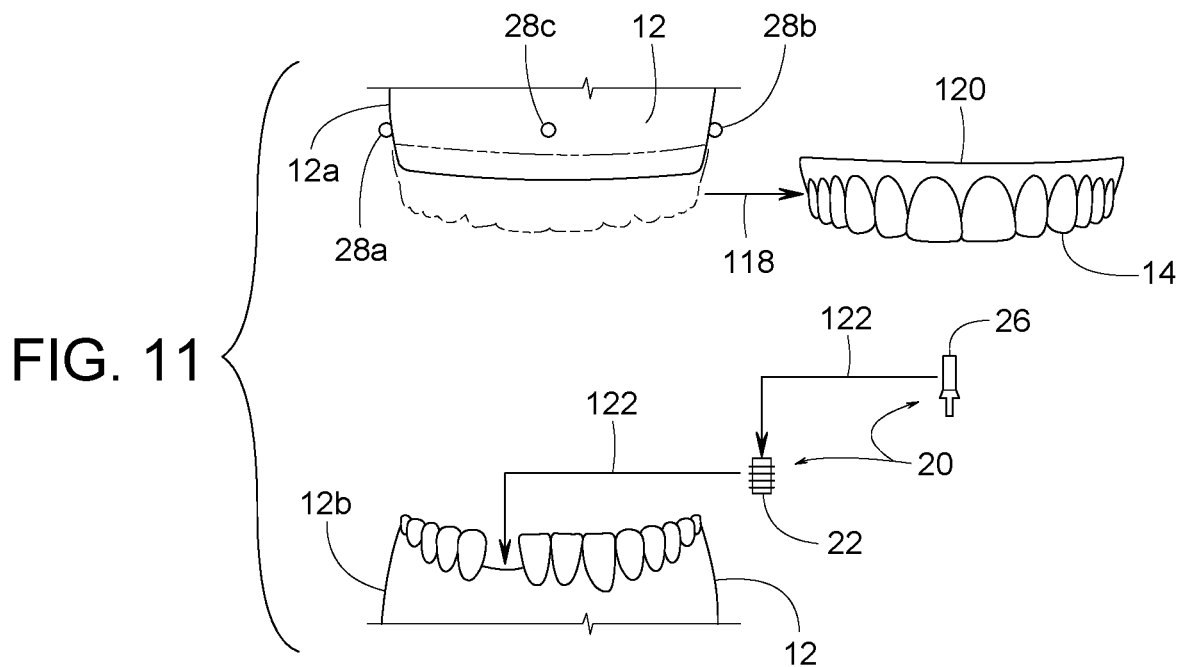
FIG. 11 is a front view showing example dental appliances being added and removed from the patient as shown in FIG. 2.
Figure 14:
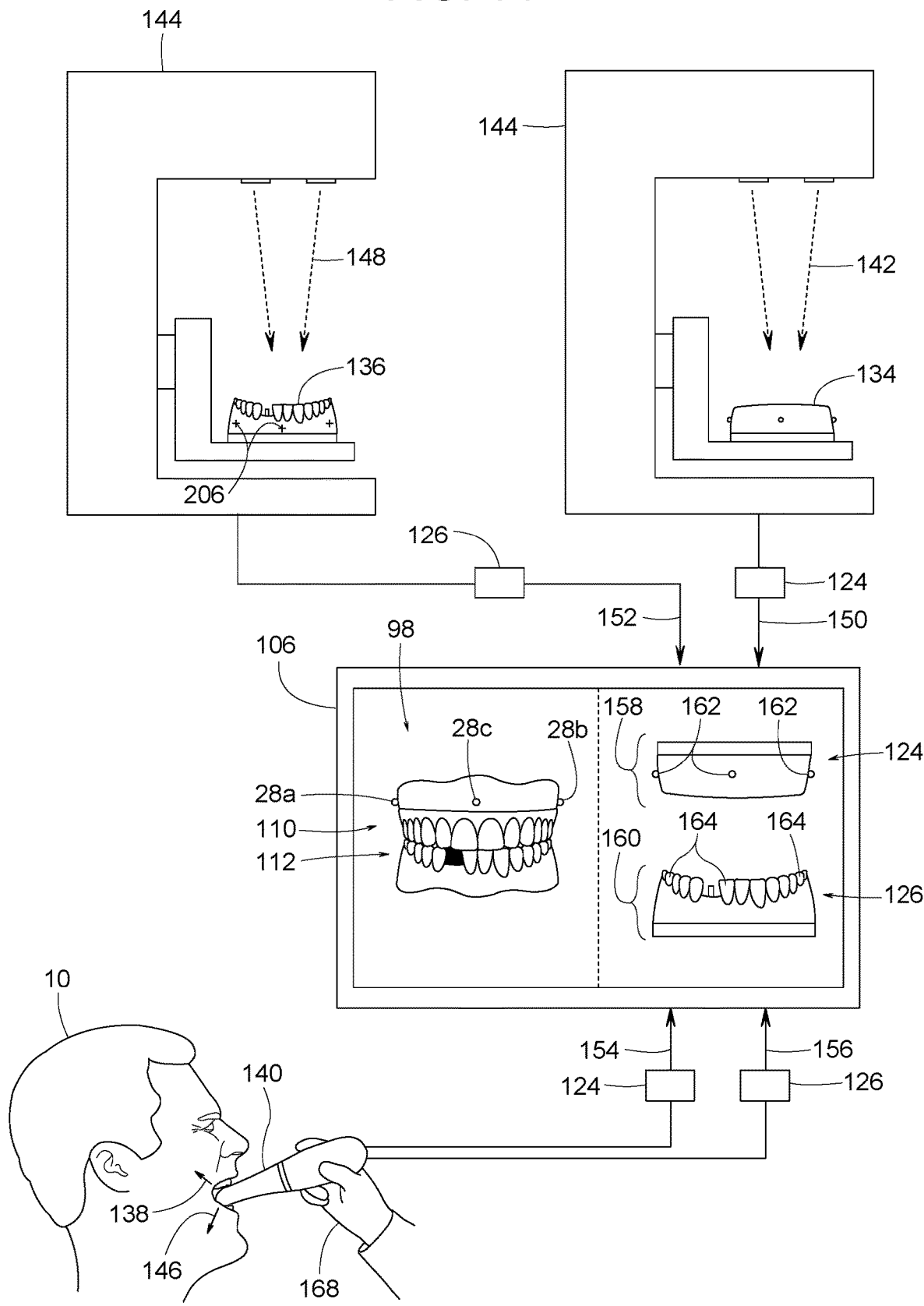
FIG. 14 is a schematic diagram showing additional example scanning methods.

Arrow 118 of FIG. 11 represents old dentures 14 being removed from the patient's upper jaw 12*a*. Since dentures 14 limit how closely jaws 12 can close, dentures 14 are considered as being a spacer 120, and arrow 118 represents removing spacer 120 from patient 10. In this example, arrows 122 represent attaching implant 20 (e.g., anchor 22 and post 26) to lower jaw 12*b*, thus arrows 122 more broadly represent attaching implant 20 to at least one of first jaw 12*a* and second jaw 12*b* and doing so after creating first scan result 98 (FIG. 10) but before creating at least one of a second scan result 124 (FIG. 14) and a third scan result 126 (FIG. 14). FIG. 10, on the other hand, shows jaws 12 being scanned while spacer 120 (e.g., old dentures 14) are still in place to help position jaws 12 at the predetermined target bite position for proper bite registration.

Figure 12:
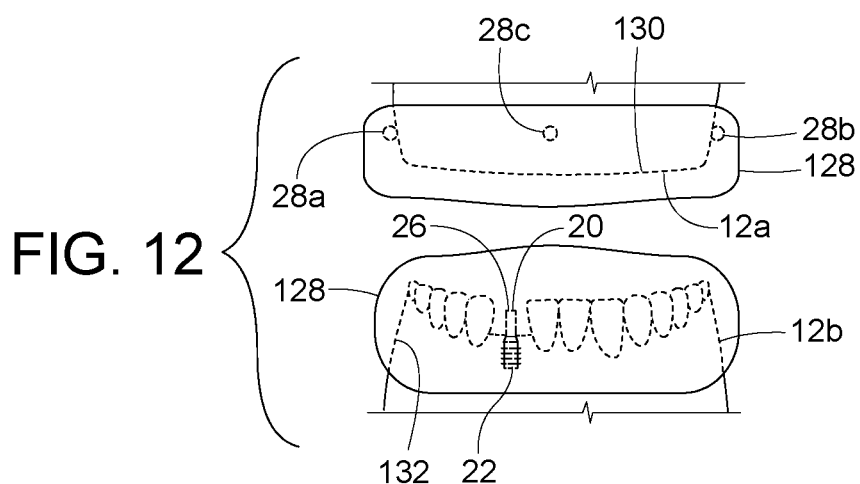
FIG. 12 is a front view showing an example method for creating cast models of the patient's jaws after the addition or removal of example dental appliances.

FIG. 12 illustrates a conventional method of using a known molding material 128 for creating molds 130 and 132 of jaws 12*a* and 12*b*, respectively. In this example, molds 130 and 132 capture the contours of jaws 12*a* and 12*b* including the shapes of implant 20; markers 28*a*, 28*b* and 28*c*; features 42*a*, 42*b* and 42*c*; the void due to the omission of dentures 14; and markers 28*d*, 28*e* and 28*f* (if used). Molds 130 and 132, however, can be independent of each other, so they do not necessarily capture the relative positions of jaws 12*a* and 12*b*.

Figure 13:
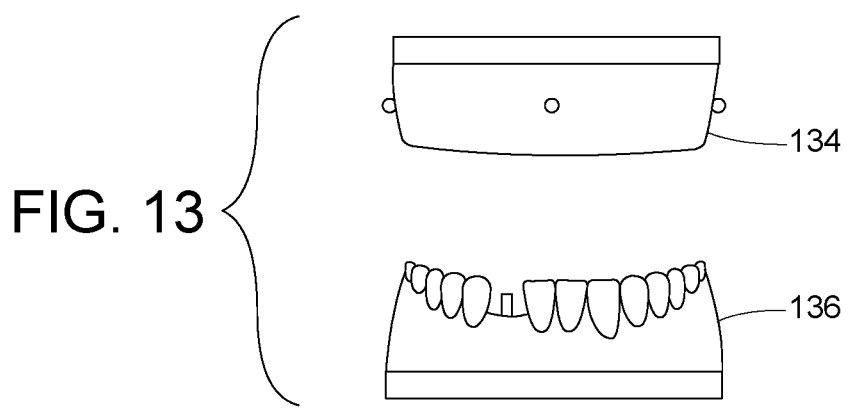
FIG. 13 is a front view of cast models created by the method shown in FIG. 12.

Molds 130 and 132 produce a physical model 134 of first jaw 12*a* and a physical model 136 of second jaw 12*b*, as shown in FIG. 13. In some examples, models 134 and 136 are castings created within the mold cavities of molds 130 and 132. Such methods of creating physical models 134 and 136 are well known to provide accurate reproductions of the surface geometries of jaws 12.

FIG. 14 illustrates creating second scan result 124 by scanning 138 first jaw 12*a* directly via a scanner 140 or scanning 142 the physical model 134 of first jaw 12*a* via a scanner 144. FIG. 14 also illustrates creating third scan result 126 by scanning 146 second jaw 12*b* directly via scanner 140 or scanning 148 the physical model 136 of second jaw 12*b* via scanner 144. Some examples of scanner 140 include a Carestream CS3600 intraoral scanner provided by Carestream Dental LLC of Rochester, New York or Atlanta, Georgia. Some examples of scanner 144 include a Medit Identica T500 benchtop scanner of Seoul, South Korea.

In some examples, using scanner 144 for scanning models 134 and 136 provides a sharper, more distinct image of individual jaws 12a and 12b than what can be achieved with scanner 102 (FIG. 10). Scanner 102, however, provides a clear representation of the jaws' relative position in their natural bite registration. So, there is a benefit to using both scanners 102 and 144, wherein scanner 102 is an example of a first scanning machine, scanner 144 is an example of a second scanning machine, and scanners 102 and 144 are two different scanning machines.

Using intraoral scanner 140 for scanning jaws 12 directly is an alternative to using scanner 144. Scanner 140 eliminates the need for creating models 134 and 136; however, scanner 140 might accumulate a series of incremental positional errors while traversing a significant distance across jaws 12. Both scanners 140 and 144 are considered "second scanning machines" and each one is different than first scanning machine 102.

Regardless of which second scanning machine 140 or 144 is used, scanners 140 and 144 generate second scan result 124 representing upper jaw 12a and third scan result 126 representing lower jaw 12b. Arrow 150 represents transmitting second scan result 124 of upper jaw model 134 from scanner 144 to computer 106, arrow 152 represents transmitting third scan result 126 of lower jaw model 136 from scanner 144 to computer 106, arrow 154 represents transmitting second scan result 124 of upper jaw 12a to computer 106, and arrow 156 represents transmitting third scan result 126 of lower jaw 12b to computer 106.

In response to receiving scan information from scanner 140 or 144, computer 106 displays second scan result 124 and third scan result 126, as shown in FIG. 14. Second scan result 124 includes a second scanned representation of the first jaw 158 and a second constellation of points 162 representing the three fiducial markers 28a, 28b and 28c. Third scan result 126 includes a second scanned representation of the second jaw 160. In some examples, third scan result 126 further includes a third constellation of points 164 representing features 42a, 42b and 42c and/or representing the second set of fiducial markers 28d, 28e and 28f.

In some examples, the first constellation of points 114, the second constellation of points 162, and/or the third constellation of points 164 are used as reference points in shifting the individual jaw images in the second scan to match the properly fitting jaw image in the first scan. In other words, shifting second scanned representation of the first jaw 158 (e.g., upper jaw 12a) relative to second scanned representation of the second jaw 160 (e.g., lower jaw 12b) so they align with first scanned representation of the first jaw 119 (e.g., upper jaw 12a) and first scanned representation of the second jaw 112 (e.g., lower jaw 12b). The goal is to shift the sharp, clear individual jaw images of jaws 12a and 12b in the second scan (FIG. 14) according to the bite registration of the first scan (FIG. 10) to create the precise digital jaw model 116 (FIGS. 20, 23 and 24) that can be manipulated and analyzed to aid in various orthodontic and other dental treatments.

FIGS. 15-20 illustrate an example of creating digital jaw model 116 (FIG. 20) by shifting (arrows 166 of FIG. 19) the second scanned representation of the first jaw 158 relative to second scanned representation of the second jaw 160 such that the second constellation of points 162 relative to the second scanned representation of the second jaw 160 substantially coincides with the first constellation of points 114 relative to the first scanned representation of the second jaw 112.

In some examples, creating an association of fiducial markers 28 and/or features 42 in the second and third scan results 124 and 126 and the corresponding fiducial markers 28 and/or features 42 in the first scan result 98, involves a dental practitioner 168 (e.g., a dentist, a lab technician, etc.) manually identifying via mouse-clicking 170 on select pairs of points of constellations 114, 162 and 164 for which associations are to be established. Constellations 114, 162 and 164 each comprise a plurality of individual points 172. Mouse-clicking 170 is one example method for manually identifying where the plurality of individual points 172 are located in space (e.g., identifying their coordinates) and for determining how far at least some of the plurality of individual points 172 should be shifted.

Figure 21:
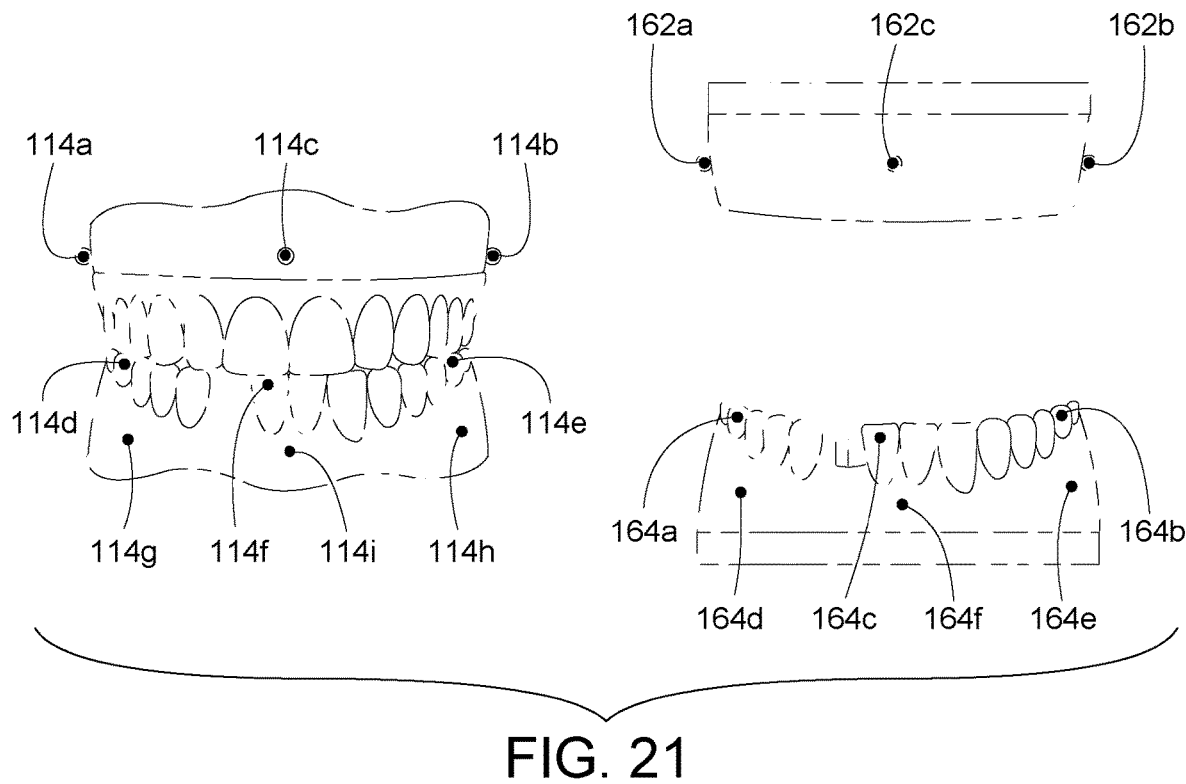
FIG. 21 is a front view of example jaw images that include some example constellations of points.

In some examples, referring to FIG. 21, first constellation of points 114 includes points 114a, 114b and 114c, which correspond to fiducial markers 28a, 28b and 28c, respectively. In addition or alternatively, some examples of first constellation of points 114 includes points 114d, 114e and 114f, which correspond to features 42a, 42b and 42c, respectively. In addition or alternatively, some examples of first constellation of points 114 includes points 114g, 114h and 114i, which correspond to fiducial markers 28d, 28e and 28f, respectively.

In some examples, second constellation of points 162 includes points 162a, 162b and 162c, which correspond to fiducial markers 28a, 28b and 28c, respectively.

In some examples of third constellation of points 164 includes points 164a, 164b and 164c, which correspond to features 42a, 42b and 42c, respectively. In addition or alternatively, some examples of third constellation of points 164 includes points 164d, 164e and 164f, which correspond to fiducial markers 28d, 28e and 28f, respectively.

In some examples, a composite constellation of points 174 comprises a combination of the second and third constellation of points 162 and 164. Some examples of the composite constellation of points 174 include points 162a, 162b and 162c plus points 164a, 164b and 164c. Some examples of the composite constellation of points 174 include points 162a, 162b and 162c plus points 164d, 164e and 164f.

Figure 15:
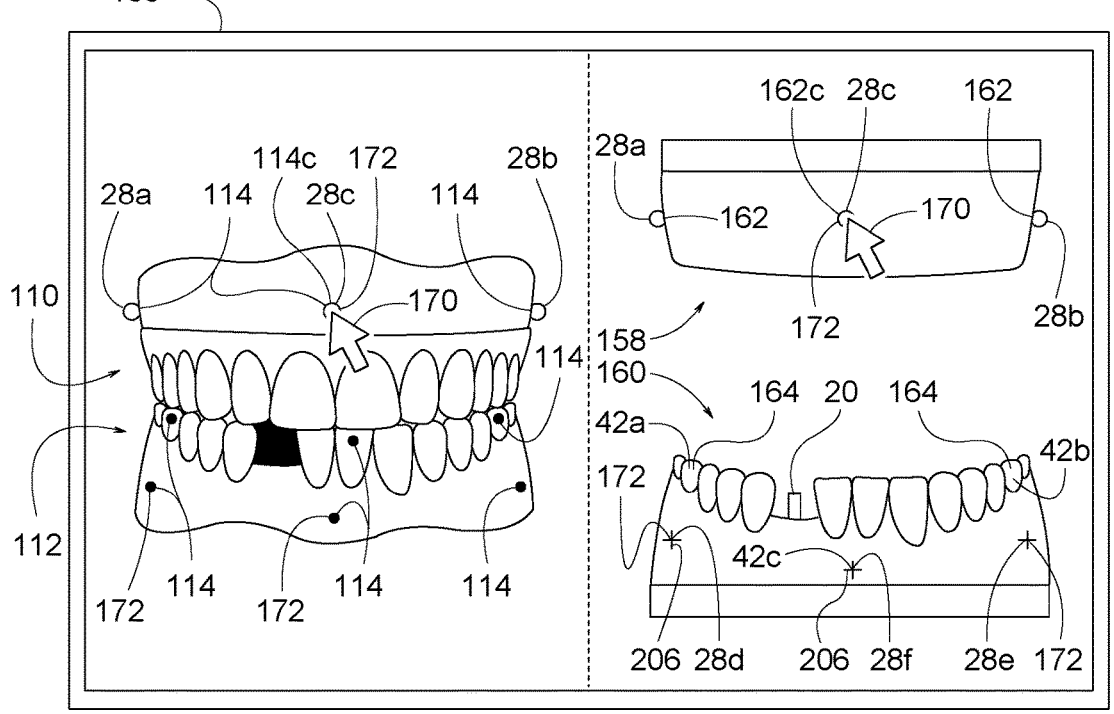
FIG. 15 is front view of a computer displaying multiple scan results of jaws and a schematic depiction of a dental practitioner mouse-clinking on certain points of the scan results.

FIG. 15 illustrates mouse-clicking 170 on point 114c of first constellation of points 114 and mouse-clicking 170 on point 162c of second constellation of points 162. In response to such mouse-clicking, computer 106 determines that points 114c and 162c represent the same point (marker 28c) on first jaw 12a.

Figure 16:
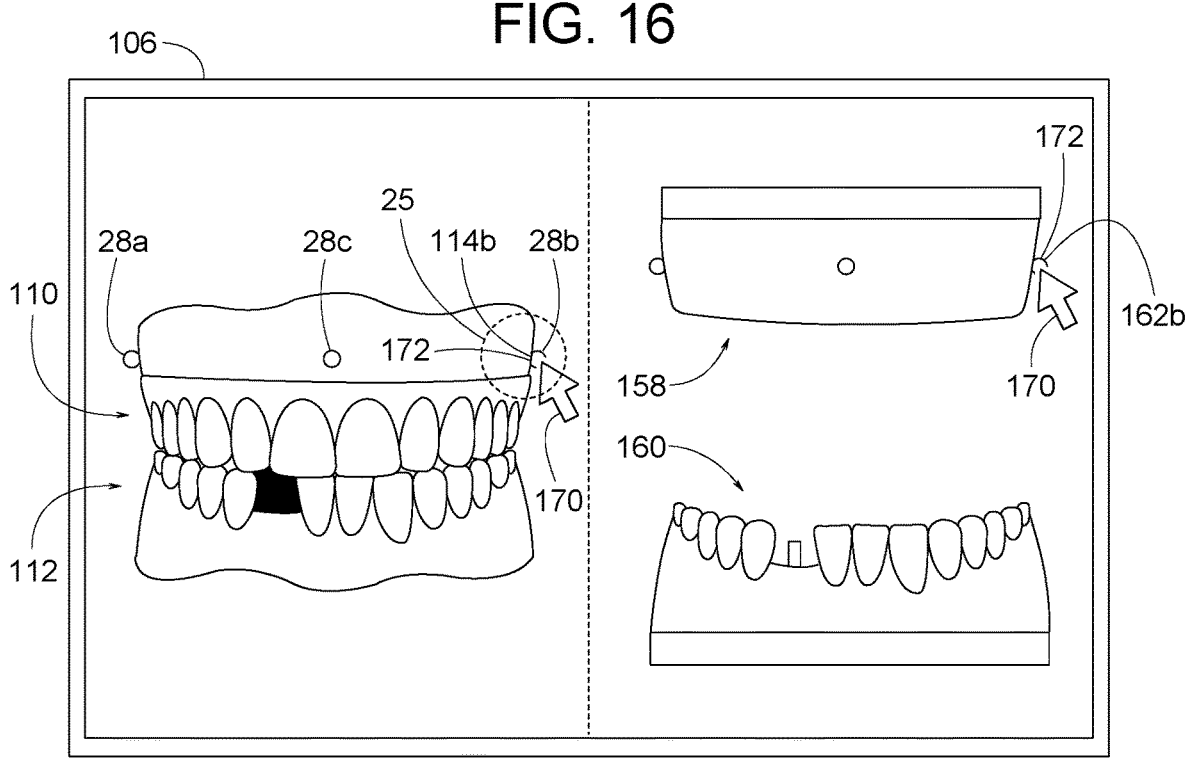
FIG. 16 is front view similar to FIG. 15 but showing a schematic depiction of the dental practitioner mouse-clinking on other points of the scan results.

FIG. 16 illustrates mouse-clicking 170 on point 114b of first constellation of points 114 and mouse-clicking 170 on point 162b of second constellation of points 162. In response to such mouse-clicking, computer 106 determines that points 114b and 162b represent the same point (marker 28b) on first jaw 12a.

Likewise, similar mouse-clicking on point 114a of first constellation of points 114 and mouse-clicking 170 on point 162a of second constellation of points 162 is interpreted as meaning that points 114a and 162a represent the same point (marker 28a) on first jaw 12a.

Figure 17:
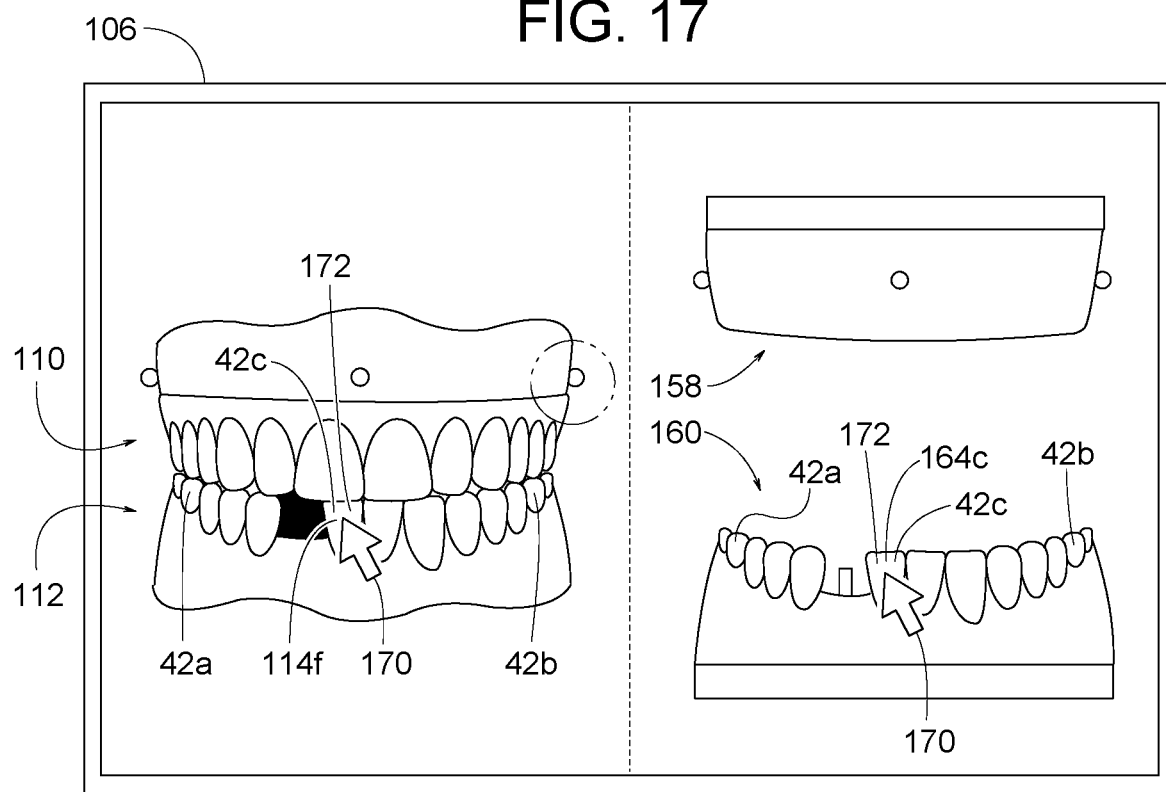
FIG. 17 is front view similar to FIG. 15 but showing a schematic depiction of the dental practitioner mouse-clinking on additional points of the scan results.
Figure 18:
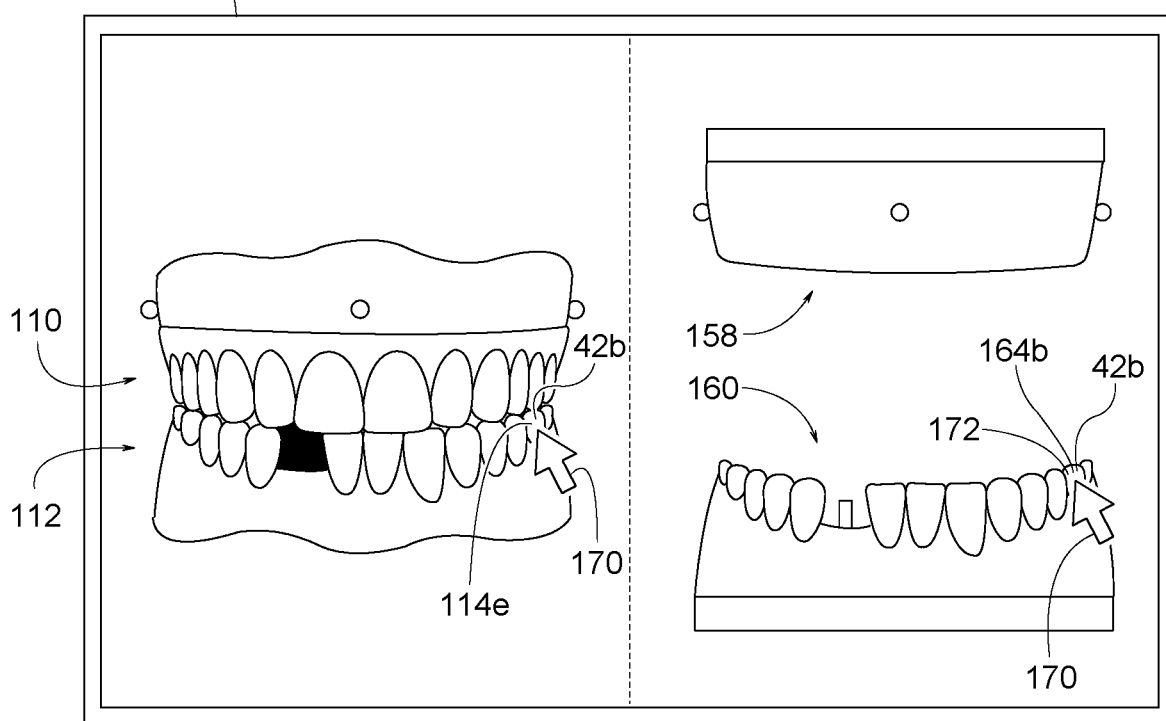
FIG. 18 is front view similar to FIG. 15 but showing a schematic depiction of the dental practitioner mouse-clinking on even more points of the scan results.

FIGS. 17 and 18 show a similar process being applied to second jaw 12b. FIG. 17 illustrates mouse-clicking 170 on point 114f of first constellation of points 114 and mouse-clicking 170 on point 164c of third constellation of points 164. In response to such mouse-clicking, computer 106 determines that points 114*f* and 164*c* represent the same point (feature 42*c*) on second jaw 12*b*.

FIG. 18 illustrates mouse-clicking 170 on point 114*e* of first constellation of points 114 and mouse-clicking 170 on point 164*b* of third constellation of points 164. In response to such mouse-clicking, computer 106 determines that points 114*e* and 164*b* represent the same point (feature 42*b*) on second jaw 12*b*. Likewise, similar mouse-clicking on point 114*d* of first constellation of points 114 and mouse-clicking 170 on point 164*a* of third constellation of points 164 is interpreted as meaning that points 114*d* and 164*a* represent the same point (feature 42*a*) on second jaw 12*b*.

The mouse-clicking method, as just described with reference to FIGS. 15-18, ties the second scan representation of the first jaw 158 (e.g., upper jaw 12*a*) to the first scan representation of the first jaw 110 (e.g., upper jaw 12*a*). Such mouse-clicking also ties the second scan representation of the second jaw 160 (e.g., lower jaw 12*b*) to the first scan representation of the second jaw 112 (e.g., lower jaw 12*b*).

Figure 19:
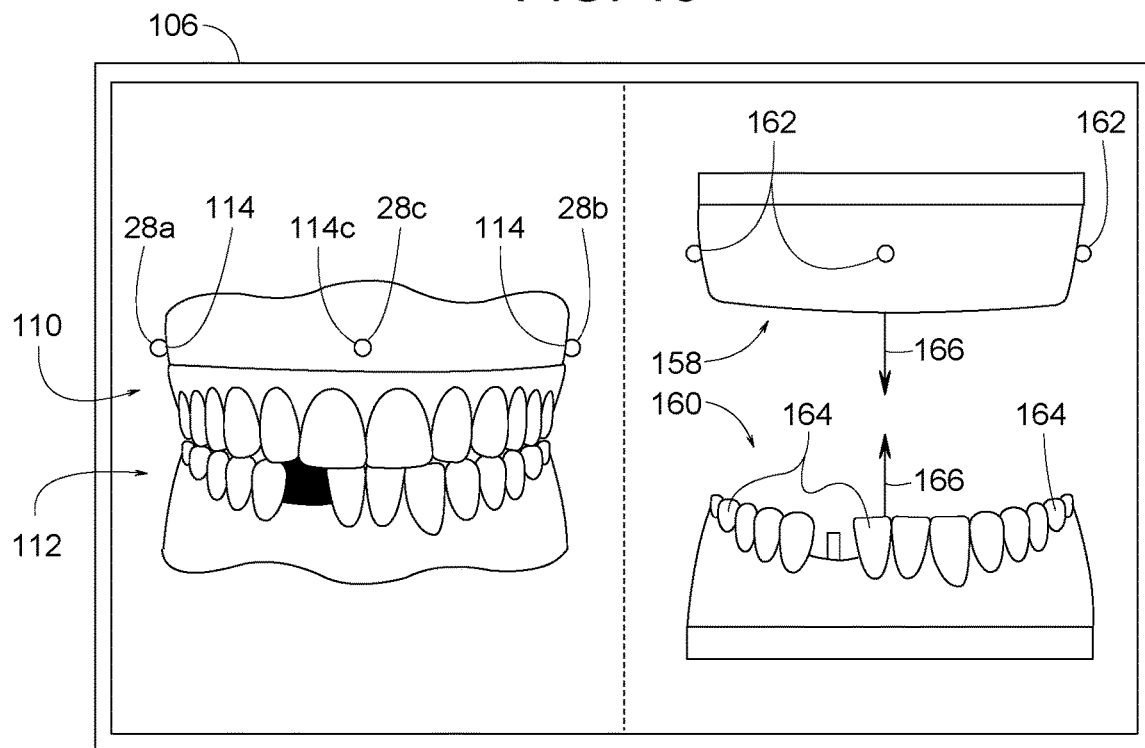
FIG. 19 is a front view similar to FIGS. 15-18 showing upper and lower jaws on the right side of the computer display being shifted to create a digital jaw model having a bite registration that matches that of the upper and lower jaws on the left side.
Figure 20:
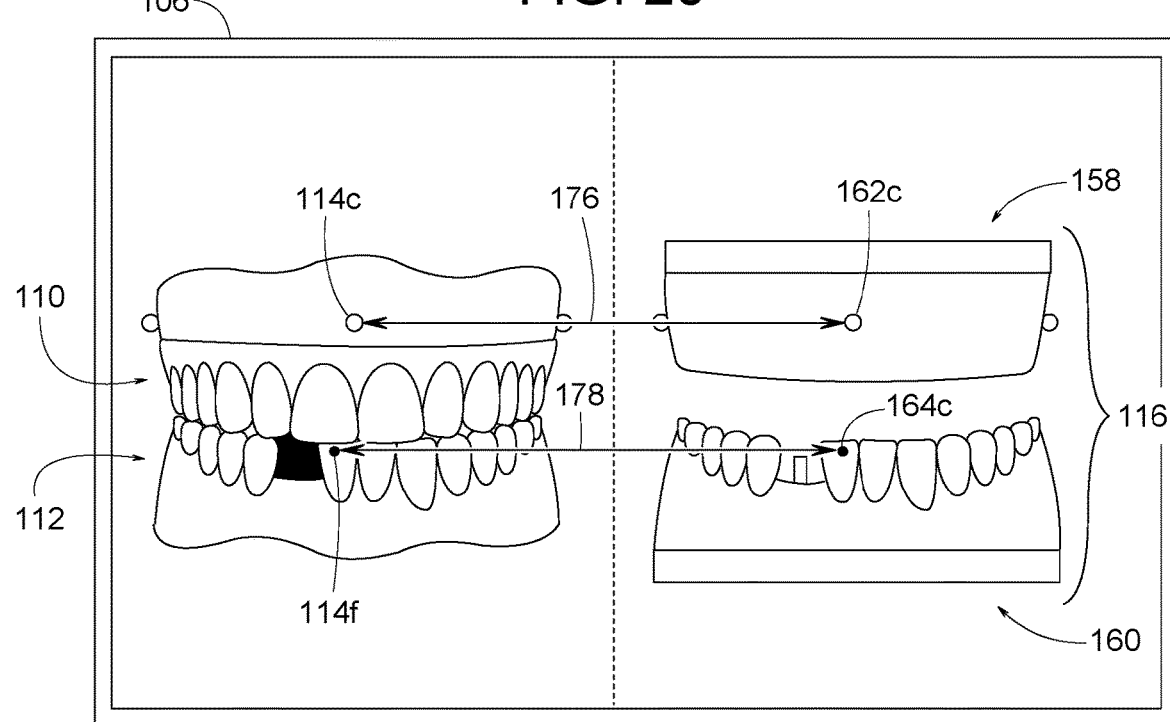
FIG. 20 is a front view similar to FIG. 19 but showing the upper and lower jaws on the right side having been shifted so as to coincide with the positional relationship of the upper and lower jaws on the left side, whereby the jaws on both sides of the display have substantially the same bite registration.

Next, as shown in FIG. 19, arrows 166 represent shifting the second constellation of points 162 and the third constellation of points 164 relative to each other such that both the second constellation of points 162 and the third constellation of points 164 of the composite constellation of points 174 substantially coincide with the first constellation of points 114. Such shifting creates digital jaw model 116, as shown in FIG. 20, arrow 176 shows how well point 162*c* of second constellation of points 162 aligns with point 114*c* of first constellation of points 114. Arrow 178 shows how well point 164*c* of third constellation of points 164 aligns with point 114*f* of first constellation of points 114. Consequently, second scan representation of the first jaw 158 and second scan representation of the second jaw 160, of digital jaw model 116, are positioned in proper bite registration in accordance with the bite registration recorded in first scan result 98.

Figure 23:
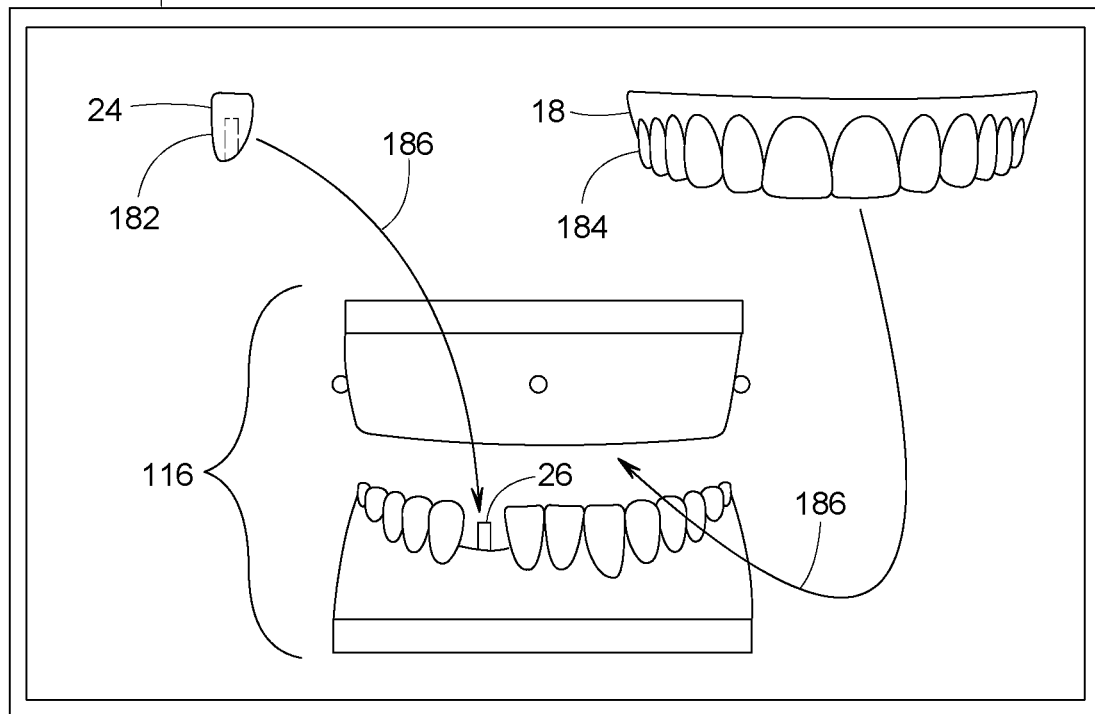
FIG. 23 is a front view of the computer displaying the recently created digital jaw model with virtual teeth and virtual dentures being fitted to the digital jaw model.
Figure 24:
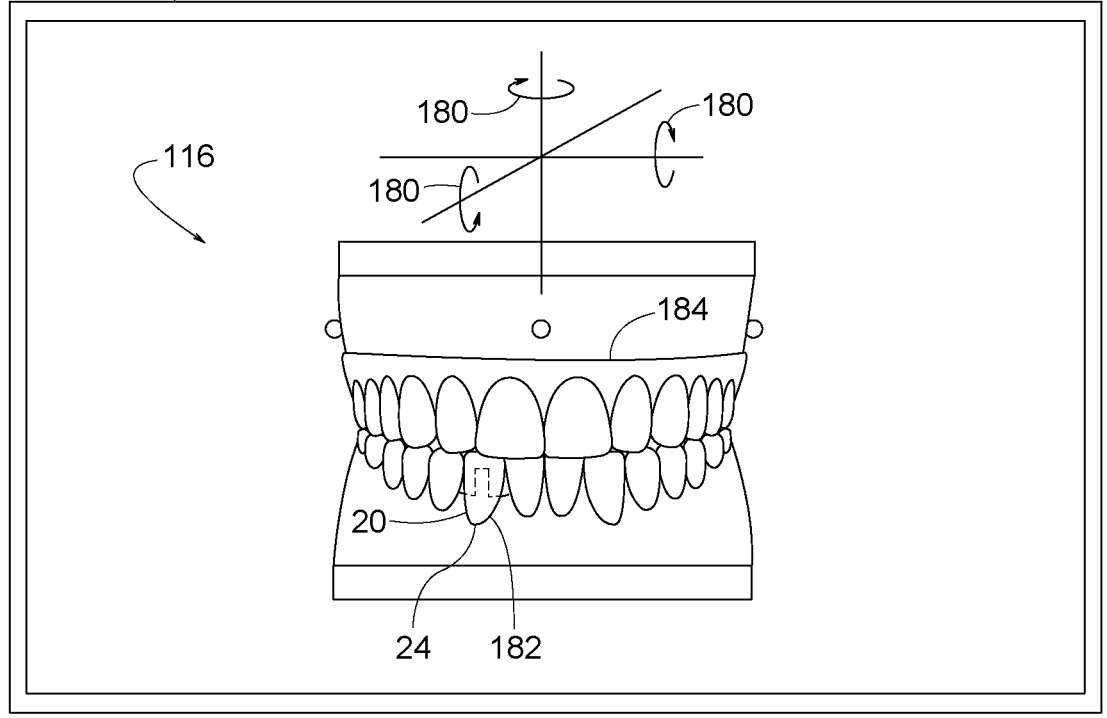
FIG. 24 is a front view similar to FIG. 23 but with the virtual dental appliances fitted in position.

Once digital jaw model 116 is configured in its proper bite registration, first scan result 98 can be set aside, and dental practitioner 168 can now focus on digital jaw model 116, as shown in FIGS. 23 and 24). To help analyze jaws 12 in the treatment of patient 10, dental practitioner 168 can view digital jaw model 116 from different angles, as known software (e.g., exocad, 3shape, dental wings, Dentsply Sirona, etc.) enables computer 106 to rotate digital jaw model 116 in virtual 3D space. Such 3D rotation is represented by arrows 180 in FIG. 24.

Figure 22:
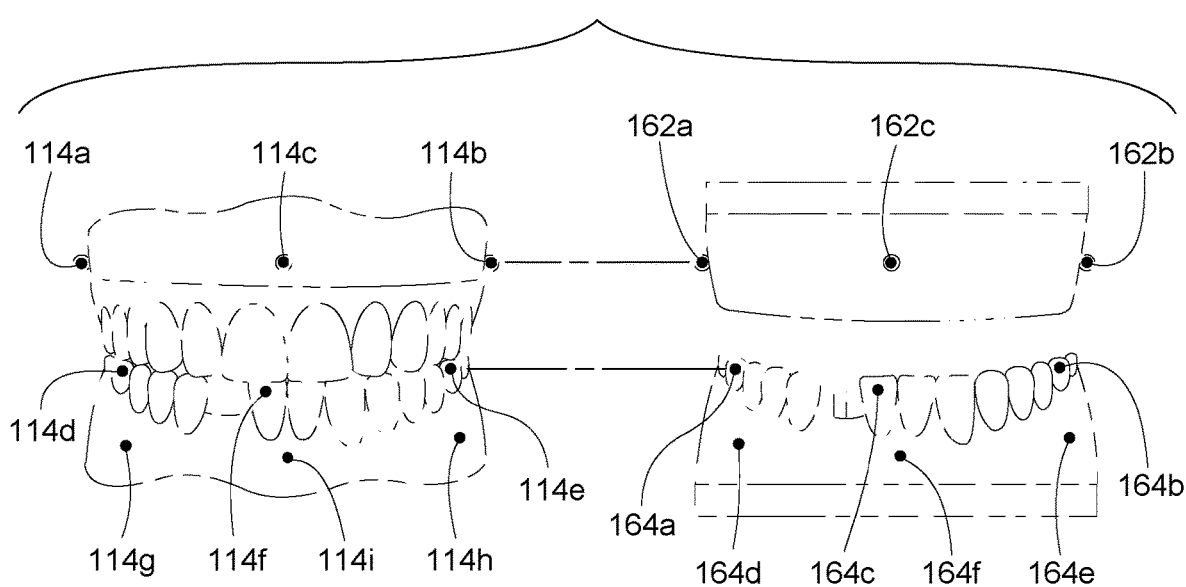
FIG. 22 is a front view similar to FIG. 21 but with some of the constellations of points shifted to another position.

In the example illustrated in FIGS. 21 and 22, dental practitioner 168 fits a virtual crown 182 (crown 24) and a virtual new set of dentures 184 (dentures 18) to digital jaw model 116. Arrows 186 of FIG. 23 represents adding a virtual dental appliance (e.g., crown 24, dentures 18, etc.) to digital jaw model 116. FIG. 24 shows the expected appearance and fit of crown 24 and dentures 18. If the appearance and fit are acceptable, dental practitioner 168 can 3D print, machine or otherwise create an actual physical crown 24 and dentures 18 that match the proposed virtual ones.

Although fiducial markers 28 can be of any suitable shape and design, FIGS. 25-27 show three examples. In FIG. 25, marker body 36 is generally spherical and is overmolded directly onto an integral extension 188 of screw 38. The slenderness of extension 188 minimizes radiographic interference with marker body 36.

In FIG. 26, marker body 36 is overmolded onto a pin 190 that is sized to fit within a blind hole 192 in screw 38. This allows marker body 36 to be attached to screw 38 for scanning and molding purposes and otherwise removed for the comfort of patient 10. In some examples, pin 190 has a shoulder 194 that ensures repeatable positioning of marker body 36 relative to screw 38. In some examples, pin 190 is tapered for tightly securing pin 190 to screw 38 and for establishing a repeatable stop position of pin 190 within a similarly tapered version of hole 192. Arrows 196 represent selectively attaching marker body 36 to screw 38 and separating marker body 36 from screw 38.

In FIG. 27, a spherical dimple 198 in head 40 of screw 38 provides a suitable surface to which a glue 200 can adhesively bond marker body 36 to head 40. A breakable adhesive bond provides a means for selectively attaching 202 marker body 36 to screw 38 and separating 204 marker body 36 from screw 38.

Here are some additional points worth noting. In FIGS. 14 and 15, marks 206 schematically represent the optional second set 58 of three fiducial markers 28*d*, 28*e* and 28*f*. Thus, arrows 146 and 148 of FIG. 14 also represents creating third scan result 126 by not only scanning at least one of the second jaw 12*b* and physical model 136 of second jaw 12*b* but by also scanning at least one of second set 58 of three fiducial markers 28*d*, 28*e* and 28*f* attached to second jaw 12*b* and physical model 136 with an indication (visual image) of the three fiducial markers 28*d*, 28*e* and 28*f* thereon.

In FIG. 10, blocks 208 represent converting first scan result 98 to a digital format substantially equal in format to that of second scan result 124 and third scan result 126. In some examples, the file converting step of block 208 is accomplished through dental treatment planning software executed by computer 106. As mentioned earlier, some examples of such software include exocad, 3shape, dental wings, and Dentsply Sirona. Some example file types include various versions of open mesh data, point cloud data, and DentalCAD HTML scenes. Some specific example file format extensions include .stl, .obj, .ply, .off, .eoff, .xyz, .xyznb.

Arrow 96 of FIG. 10 illustrates creating first scan result 98 by concurrently scanning 100 first jaw 12*a* and second jaw 12*b* of patient 10. FIG. 14 illustrates creating second scan result 124 by scanning (arrows 138 and 142) at least one of first jaw 12*a* and physical model 134 of first jaw 12*a*, wherein creating first scan result 98 is accomplished using first scanning machine 102, creating second scan result 124 is accomplished using second scanning machine 144, and first scanning machine 102 and second scanning machine 144 are two different machines. FIG. 14 also illustrates creating third scan result 126 by scanning (arrows 146 and 148) at least one of second jaw 12*b* and physical model 136 of second jaw 12*b*.

Computer 106 in FIG. 14 illustrates displaying first scan result 98 including first scanned representation of the first jaw 110 (upper jaw 12*a*) and first scanned representation of the second jaw 112 (lower jaw 12*b*) in a first positional relationship relative to each other (e.g., jaws 12 in a predetermined proper bite registration). Computer 106 in FIG. 14 illustrates displaying second scan result 124 including second scanned representation of the first jaw 158. Computer 106 in FIG. 14 illustrates displaying third scan result 126 including second scanned representation of the second jaw 160 in a second positional relationship (e.g., jaws 12*a* and 12*b* widely spaced apart) relative to second scanned representation of the first jaw 158.

Arrows 166 of FIG. 19 illustrates shifting second scanned representation of the first jaw 158 relative to second scanned representation of the second jaw 160 such that the second positional relationship of second scanned representation of the first jaw 158 relative to the second scanned representation of the second jaw 160 is substantially equal to (as indicated by arrows 176 and 178 of FIG. 20) the first positional relationship of the first scanned representation of the first jaw 110 relative to the first scanned representation of the second jaw 112.

Arrow 118 of FIG. 11 illustrates removing at least one of a tooth and a dental appliance (e.g., dentures 14) from patient 10 after creating first scan result 98 but before creating second scan result 124. Otherwise, failing to remove such items would interfere with second scan result 124 and/or third scan result 126 and thus interfere with planning of the patient's treatment.

FIGS. 28-48 illustrate examples that can be used in addition or as alternatives to the examples already described and illustrated in FIGS. 1-27. FIGS. 28-37 show a method for analyzing a scan result 210 (e.g., scan result 98, 124, and/or 126) of fiducial marker 28 attached to jaw 12 of patient 1, wherein the method involves the use of computer 106 and a user (e.g., dental practitioner 168) providing a user input 212 (e.g., mouse clicking 170, keyboard entry, etc.).

In the example of FIGS. 28-37, the method involves computer 106 executing digital image analytics 214 (FIG. 37) to accurately identify a location or center point of a fiducial marker 28 that might appear blurring in the scan image due to a scanning problem known as "scatter." The term, "digital image analytics" refers to an algorithm executed by a computer for making a pixel-by-pixel evaluation of a digital image. In some but not all examples, digital image analytics does a pixel-to-pixel comparison of two digital images. Such a comparison can be used by the computer for iteratively adjusting the position, orientation and/or size of one image relative to the other to minimize the differences between the two.

Figure 28:
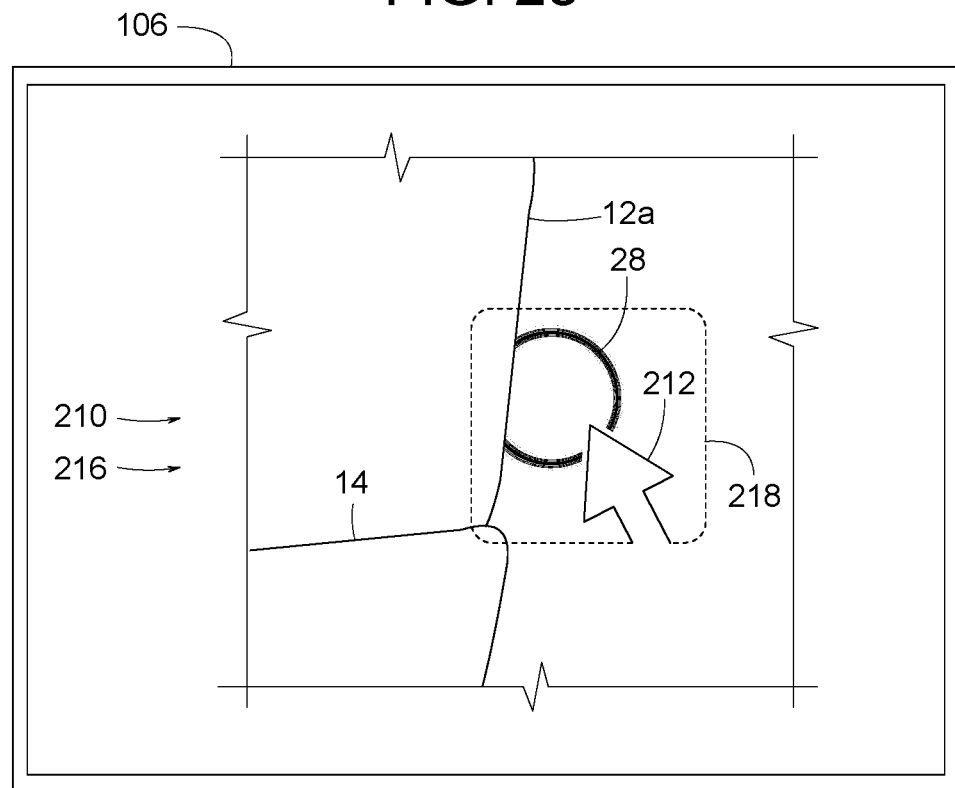
FIG. 28 is an enlarged view of area 25 identified in FIG. 16 and as viewed along a Z-axis (FIG. 36).
Figure 29:
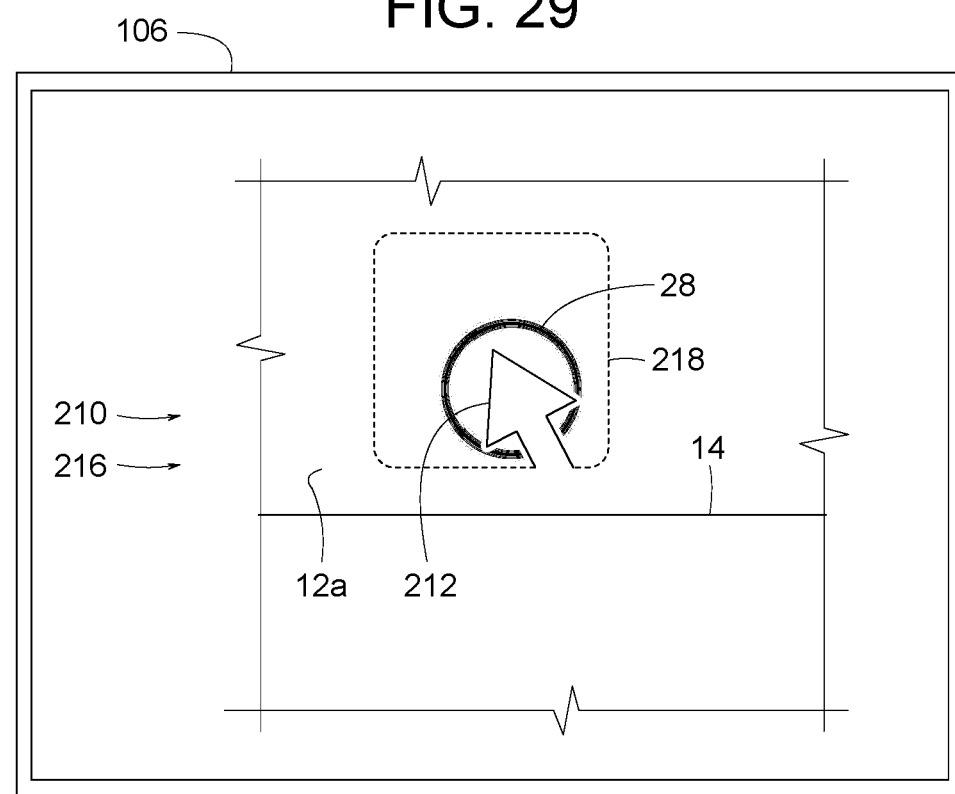
FIG. 29 is an enlarged view similar to FIG. 28 but as viewed from another perspective, i.e., as viewed along an X-axis (FIG. 36)

FIG. 28 illustrates displaying, via computer 106, a first perspective of scan result 210 including a scan representation 216 (e.g. scan representations 110, 112, 158 and 160) of fiducial marker 28. FIG. 29 illustrates displaying, via the computer 106, a second perspective of scan result 210 including scan representation 216 of fiducial marker 28. In the illustrated example, fiducial marker 28 appears blurry due to scatter and/or limited scanning accuracy.

FIGS. 28 and 29 illustrate identifying on scan result 210, via user input 212, a general location 218 of fiducial marker 28 as viewed from the first and second perspectives, FIGS. 28 and 29 respectively.

Figure 30:
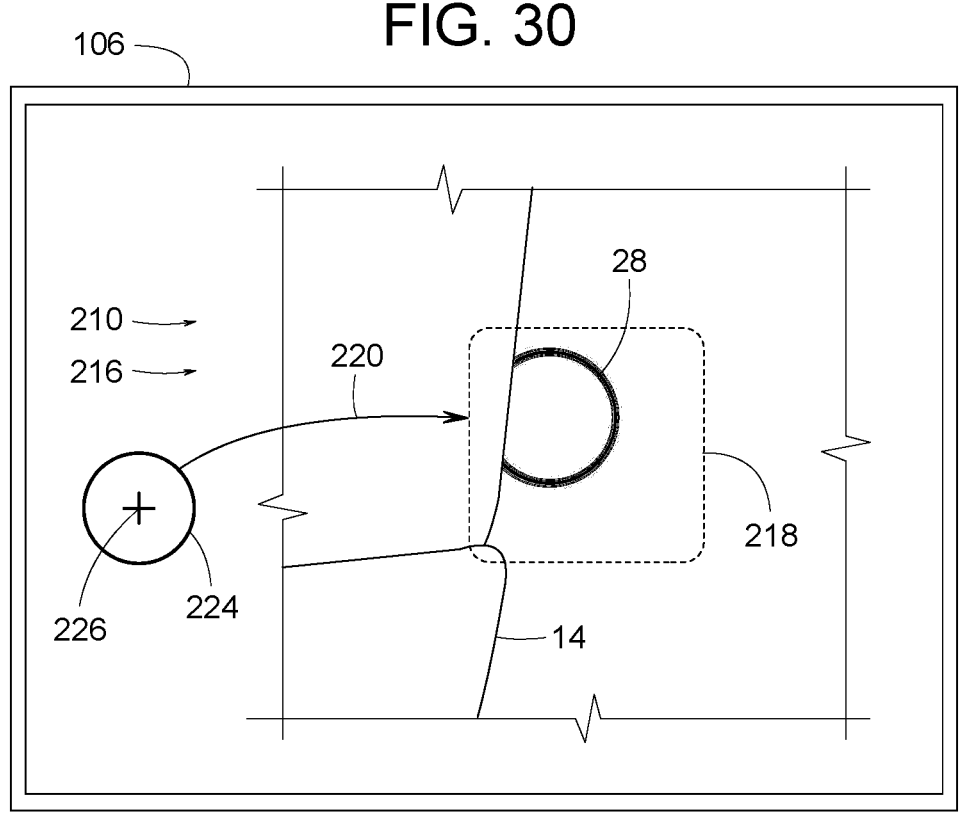
FIG. 30 is a view similar to FIG. 28 but further showing the assignment of a geometric feature.
Figure 31:
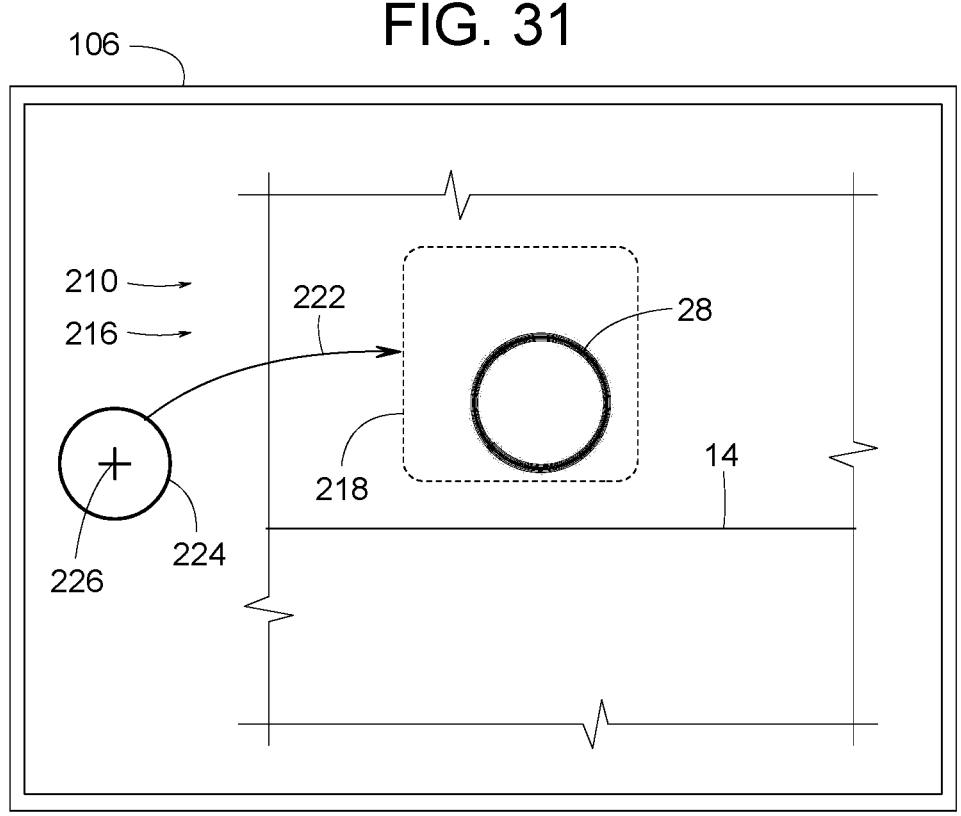
FIG. 31 is a view similar to FIG. 29 but further showing the assignment of the geometric feature.

Arrows 220 and 222 of FIGS. 30 and 31, respectively, represent assigning a geometric feature 224 (e.g., a circle, a sphere, a predefined key point 226 such as a center point, etc.) to scan representation 216 of fiducial marker 28 in the general location 218 identified by user input 212, wherein the geometric feature 224 includes predefined key point 226. In some examples, user 168 provides computer 106 with a user input via keyboard identifying marker 28 by size (e.g., diameter) or by part/model number.

Figure 32:
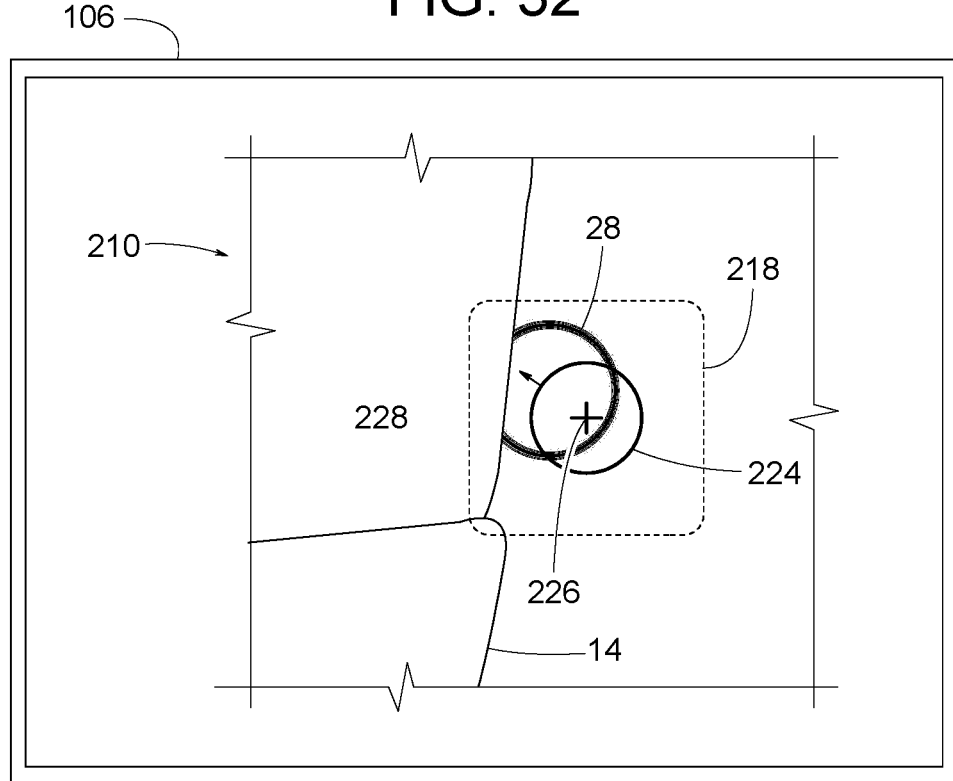
FIG. 32 is a view similar to FIGS. 28 and 30 but further showing the geometric feature being moved into alignment with a marker body.
Figure 33:
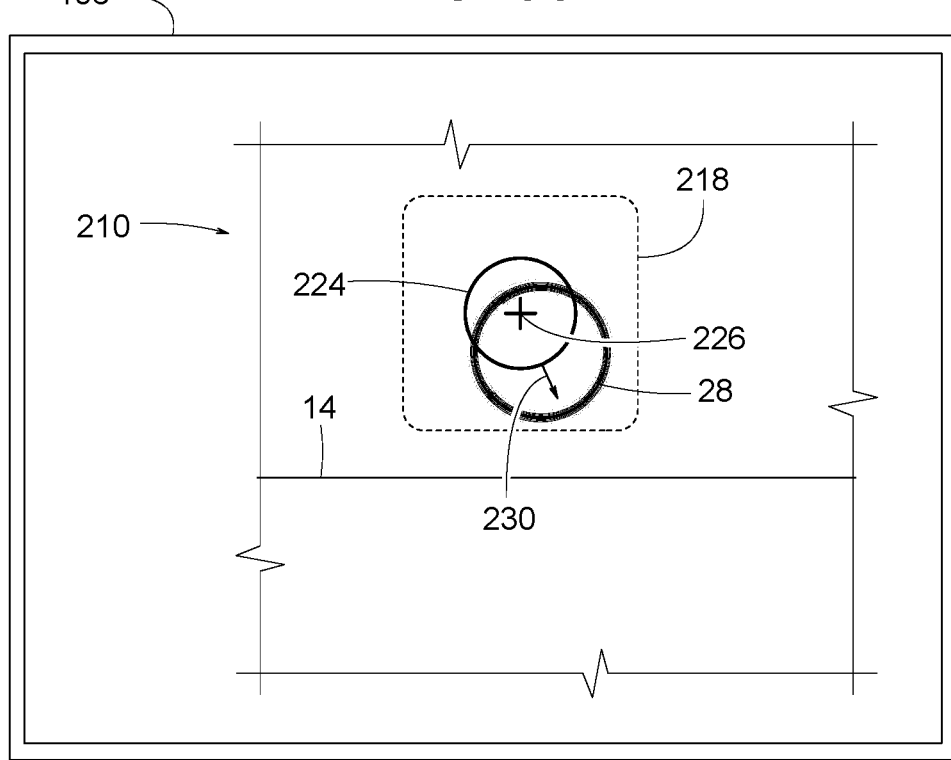
FIG. 33 is a view similar to FIGS. 29 and 31 but further showing the geometric feature being moved into alignment with the marker body.

Arrows 228 and 230 of FIGS. 32 and 33 illustrate aligning, via computer 106 executing digital image analytics, the geometric feature 224 to the scan representation of fiducial marker 28.

Figure 34:
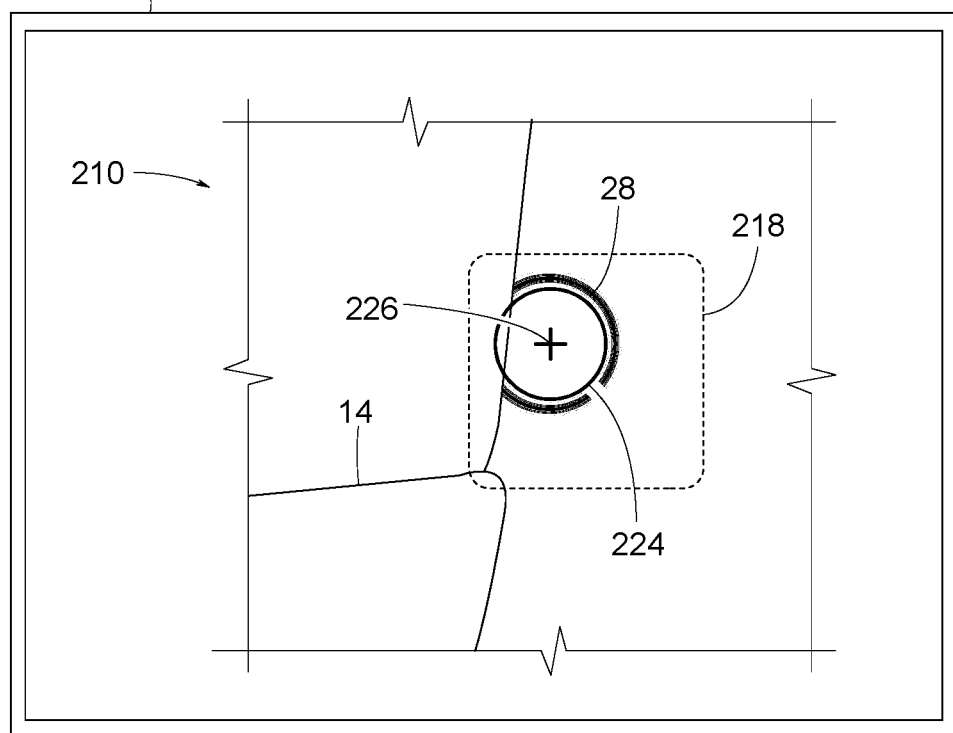
FIG. 34 is a view similar to FIG. 32 but showing the geometric feature aligned with the marker body.
Figure 35:
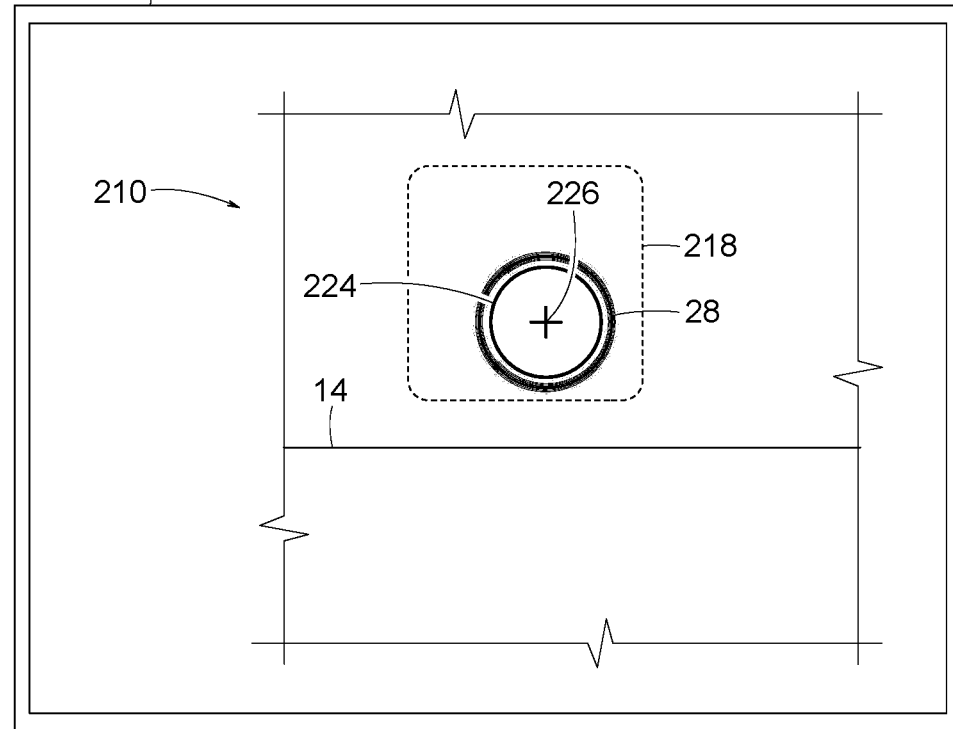
FIG. 35 is a view similar to FIG. 33 but showing the geometric feature aligned with the marker body.

FIGS. 34 and 35 show the results of assigning the predefined key point 226 to the general location 218 of fiducial marker 28, whereby the predefined key point 226 provides a more precise location of fiducial marker 28. In the future, then, whenever user 168 mouse-clicks anywhere within general location 218, computer 106 assumes the user 168 is really trying to more precisely select the predefined key point 226 now assigned to fiducial marker 28.

Figure 36:
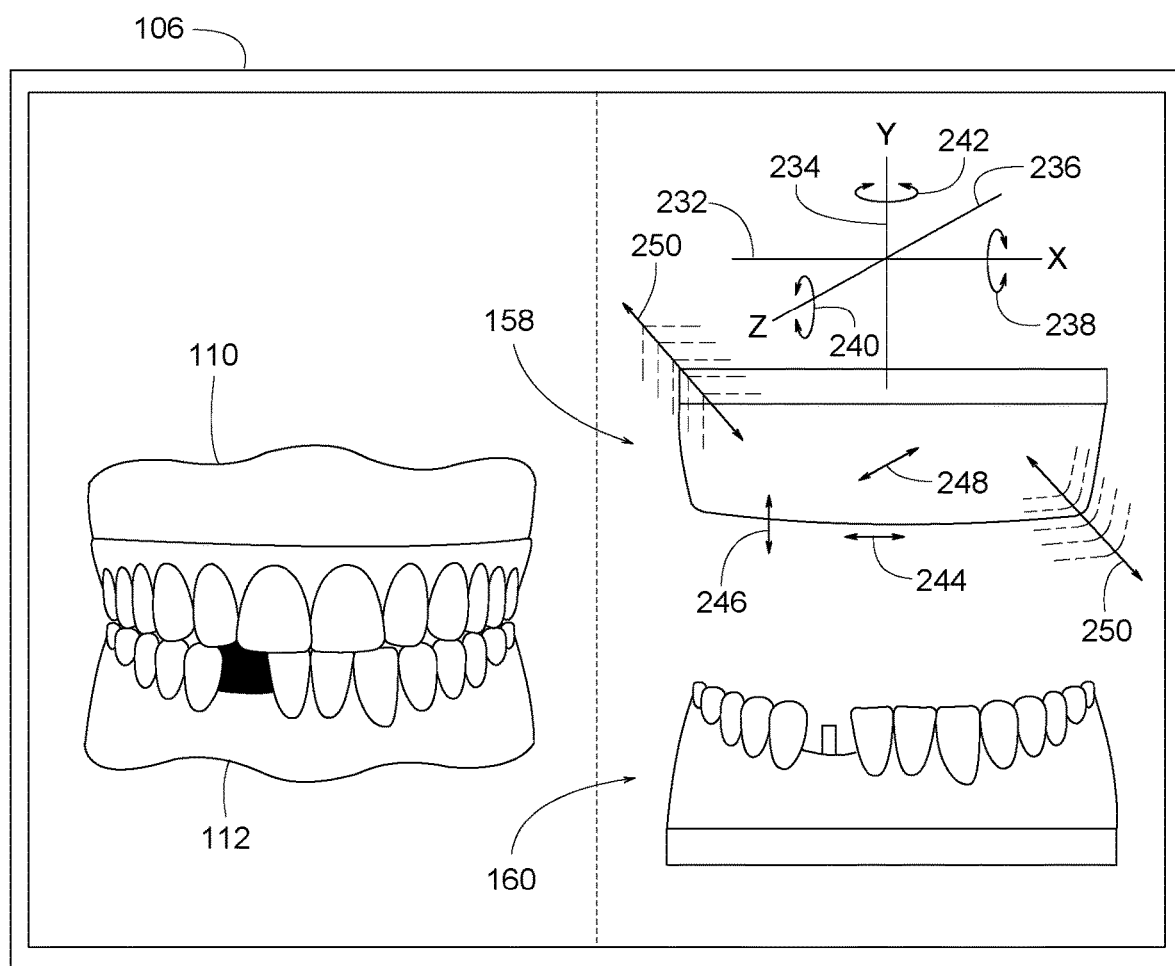
FIG. 36 is a front view similar to FIG. 15 but showing one of the scan results being adjusted in various dimensions.

In the example shown in FIGS. 36 and 37, scan results are iteratively adjusted in dimensions of scale (size), orthogonal position and angular orientation till the two scan results (e.g., scans 110 and 158, scans 112 and 160, etc.) most closely match by those dimensions. FIG. 36 shows an X-axis 232, a Y-axis 234, a Z-axis 236, a pitch 238 about X-axis 232, a roll 240 about Z-axis 236, and a yaw 242 about Y-axis 234. Arrows 244, 246 and 248 represent adjusting along X-axis 232, Y-axis 234, and Z-axis 236, respectively. Arrows 250 represent adjustments in size or scale. FIG. 37 illustrates method steps 214 performed by image analytic software executed by computer 106.

In some examples, user 168 provides computer 106 with limits as to how far computer 106 can scale and shift an image. In some examples, computer 106 provides an error message if computer 106 determines that an "optimized" adjustment occurs at or beyond such a user-specified limit. In some examples, user 168 does initial visual adjustments to get it in the "ballpark," and computer 168 later applies digital image analytics for final, more precise adjustments. In some examples, the method illustrated in FIG. 37 can be used with or without fiducial markers 28.

FIGS. 38-43 illustrate another example fiducial marker system and method for analyzing jaw 12. This example involves using a rubbery molding material 128 and a casting material 252 (e.g., plaster, cement, epoxy, ceramic, etc.) for creating a cast model 254 (e.g., model 134 or 136).

Figure 38:
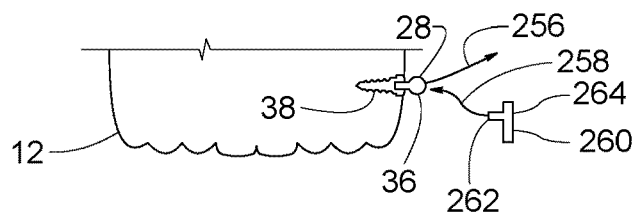
FIG. 38 is a schematic diagram illustrating a method steps step for analyzing jaws of a patient.

Referring to FIGS. 38-43 and other previously described figures, arrow 48 (FIG. 4) represents attaching fiducial marker 28 to jaw 12, wherein fiducial marker 28 comprises marker body 36 attached to screw 38. Arrow 100 of FIG. 10 represents scanning jaw 12 and fiducial marker 28 attached thereto. Arrow 256 of FIG. 38 represents removing marker body 36 from screw 38. Arrow 258 of FIG. 38 represents attaching a holder 260 to screw 38, wherein holder 260 has a first end 262 and a second end 264. Holder 260 can be of any desired shape and design but is preferably larger than marker body 36, so holder 260 can be securely embedded in molding material 128.

Figure 39:
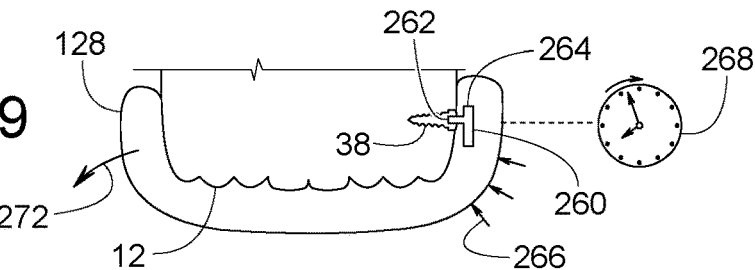
FIG. 39 is a schematic diagram illustrating another method step for analyzing jaws of a patient.

Arrows 266 of FIG. 39 represents applying molding material 128 to jaw 12 and to the holder's second end 264 while the holder's first end 262 is still attached to screw 38. Clock 268 represents allowing molding material 128 to set while on jaw 12, thereby creating a rubbery mold (e.g., mold 130 or 132) that defines a mold cavity 270. Arrows 266 and clock 268 also represent encasing the holder's second end 264 within molding material 128 while allowing molding material 128 to set.

Figure 40:
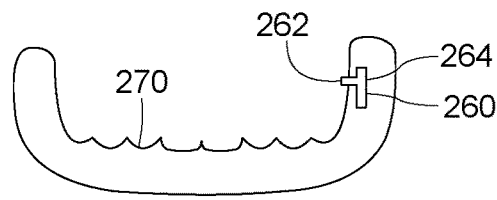
FIG. 40 is a schematic diagram illustrating another method step for analyzing jaws of a patient.

Arrow 272 of FIG. 39 represents separating the holder's first end 262 from screw 38 by removing molding material 128 and holder 260 from jaw 12 while the holder's second end 264 remains encased within molding material 128. FIG. 40 shows the resulting mold (e.g., mold 130 or 132) with the holder's second end 264 is encased therein.

Figure 41:
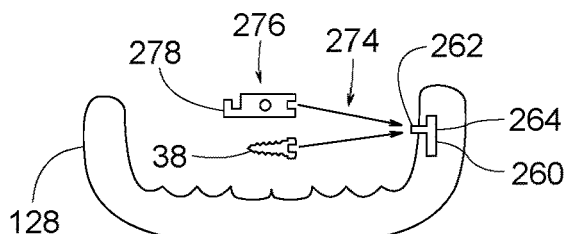
FIG. 41 is a schematic diagram illustrating another method step for analyzing jaws of a patient.

Arrows 274 of FIG. 41 represent attaching an anchor 276 to the holder's first end 262 while the holder's second end 264 remains encased within molding material 128. The term, "anchor" refers to any structure that can be embedded within casting material 252 and provide some means for which something else can be attached thereto. Some examples of anchor 276 include screw 38 and any other conceivable member 278.

Figure 42:
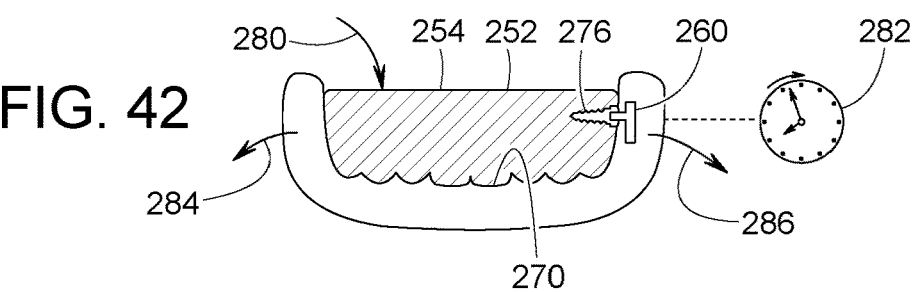
FIG. 42 is a schematic diagram illustrating another method step for analyzing jaws of a patient.

Arrow 280 of FIG. 42 represents filling mold cavity 270 with casting material 252 and thereby encasing anchor 276 within casting material 252 while filling mold cavity 270 with casting material 252. Clock 282 of FIG. 42 represents allowing casting material 252 to set. Arrow 284 of FIG. 42 represents removing casting material 252 from within the mold cavity 270 while anchor 276 remains encased within casting material 252. Arrow 286 of FIG. 42 represents removing holder 260 from anchor 276 by removing the mold (e.g., mold 130 or 132) from the hardened casting material 252.

Figure 43:
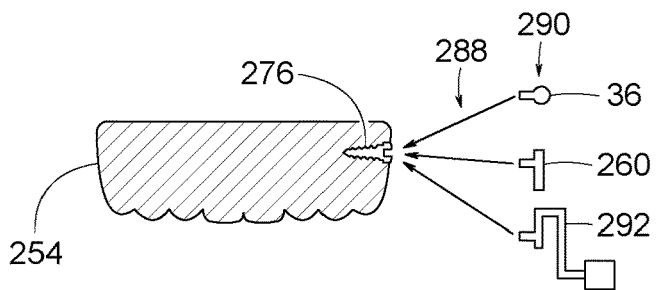
FIG. 43 is a schematic diagram illustrating another method step for analyzing jaws of a patient.

Arrows 288 of FIG. 43 represent attaching a piece 290 to anchor 276 where the holder's first end 262 was previously attached to anchor 276. Examples of piece 290 include marker body 36 (or some resemblance thereof), holder 260 (or some resemblance thereof), and any other conceivable tool or fixture 292 that might prove useful in various dental treatments.

Figure 44:
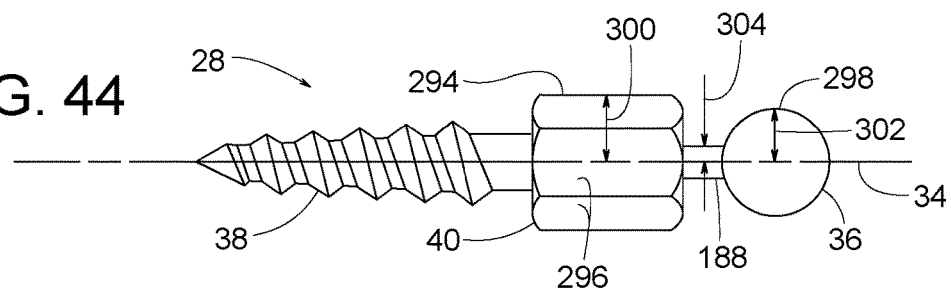
FIG. 44 is a side view of an example fiducial marker constructed in accordance with the teachings disclosed herein.

Some examples of fiducial marker 28, as shown in FIG. 44, head 40 has a head outer perimeter 294 with a plurality of faces 296. The plurality of faces 296 face radially outward from longitudinal axis 34 to be drivingly engaged by a suitable tool (e.g., a wrench). In some examples, screw 38 and head 40 are made of a monolithic piece of a first material (e.g., a metal). Example geometries of head 40 include a six-sided prism (hexagonal cross-section), a four-sided prism (square cross-section), a star prism (e.g., Torx head), etc.

Still referring to FIG. 44, marker body 36 has a marker outer perimeter 298 and is made a second material (e.g., a polymer) distinguishable from the first material of screw 38. In some examples, second material is polymethyl methacrylate (e.g., PMMA or acrylic) impregnated with 10% (by volume) barium sulfate, so marker body 36 is substantially radiopaque.

In the illustrated example, extension 188 connects marker body 36 to head 40 of screw 38, such that screw 38, head 40, marker body 36 and extension 188 are coaxially aligned with longitudinal axis 34. To facilitate the installation and removal of fiducial marker 28, head outer perimeter 294 extends a first radial distance 300 from longitudinal axis 34, marker outer perimeter 298 extends a second radial distance 302 from longitudinal axis 34, and first radial distance 300 is greater than second radial distance 302. In some examples, marker body 36 is one to three millimeters in diameter for greater positional accuracy. In some examples, to minimize certain scanning distortion or scatter, extension 188 extends a third radial distance 304 from longitudinal axis 34, wherein third radial distance 304 is less than second radial distance 302.

Figure 45:
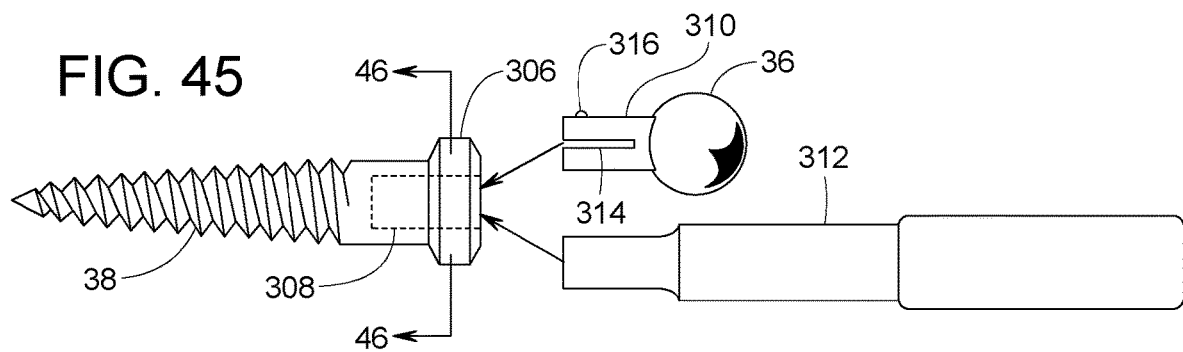
FIG. 45 is an exploded side view illustrating the interchangeability a tool and a marker body with a screw.
Figure 46:
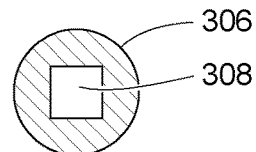
FIG. 46 is a cross-sectional view taken along line 46-46 of FIG. 45.
Figure 47:
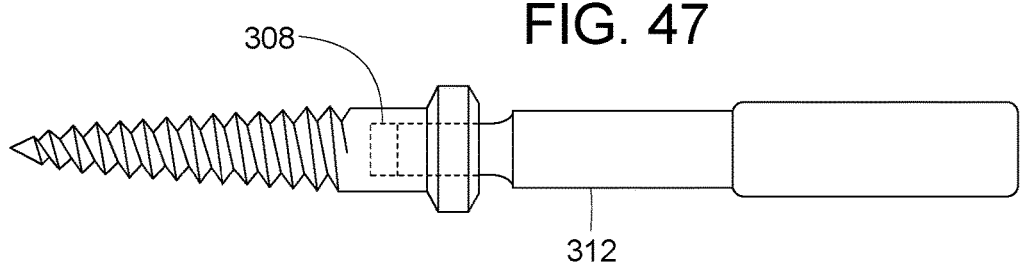
FIG. 47 is a side view similar to FIG. 45 but showing the tool attached to the screw.
Figure 48:
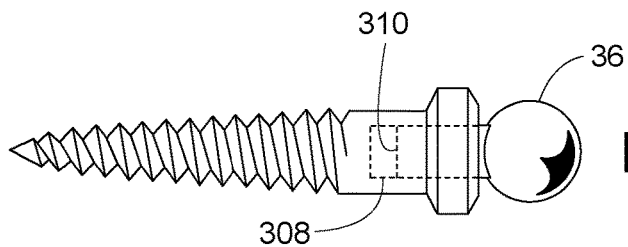
FIG. 48 is a side view similar to FIG. 45 but showing the marker body attached to the screw.

Some examples of fiducial marker 28, as shown in FIGS. 45 and 46, have a head 306 on screw 38 that are of a monolithic piece of a first material (e.g., a metal) with a socket 308 in head 306. Socket 308 is of a size and shape (e.g., square) to matingly engage with and to receive selectively an extension 310 of marker body 36 or a tool 312 for installing or removing screw 38 from jaw 12. FIG. 47 shows tool 312 inserted into socket 308, and FIG. 48 shows extension 310 inserted into socket 308.

In some examples, marker body 36 is made of a second material (a polymer) that is distinguishable from the first material of screw 38, thereby making marker body 36 easier to identify in a scan result. In some examples, extension 310 includes a slot 314 that enables extension 310 to resiliently flex and snuggly fit in socket 308. In some examples, extension 310 includes a protrusion 316 that helps secure extension 310 to head 306 of screw 38.

To minimize scatter distortion in scan results, some examples of fiducial marker 28 have extension 188 (or extension 310) be less radiopaque than marker body 36. In some examples, extension 188 is made of a polymeric extension material with virtually no barium sulfate, while marker body 36 is made of a second polymeric material with 10% barium sulfate. In some examples where extension 188 and marker body 36 are made of different materials, the two materials (the marker body's polymer with barium sulfate and the extension's polymer without barium sulfate) are co-molded as a unitary but nonmonolithic piece. The process of co-molding is also known as overmolding, multi-material injection molding, and MMM.

Figure 49:
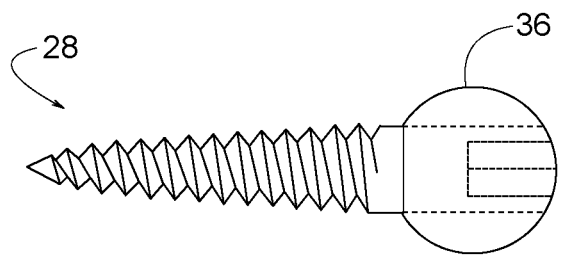
FIG. 49 is a side view of another example fiducial marker.
Figure 50:
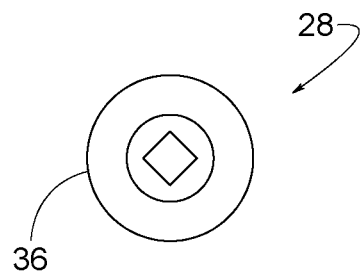
FIG. 50 is a right end view of FIG. 49

FIGS. 49-69 illustrate various items and methods that, in some examples, can be used as alternatives to the items and methods shown in FIGS. 38-43. FIGS. 49 and 50 show another example of fiducial marker 28. In this example, marker body 36 is on head 315 of screw 38. A socket 325 in head 315 enables screwing screw 38 into jaw 12.

Figure 51:
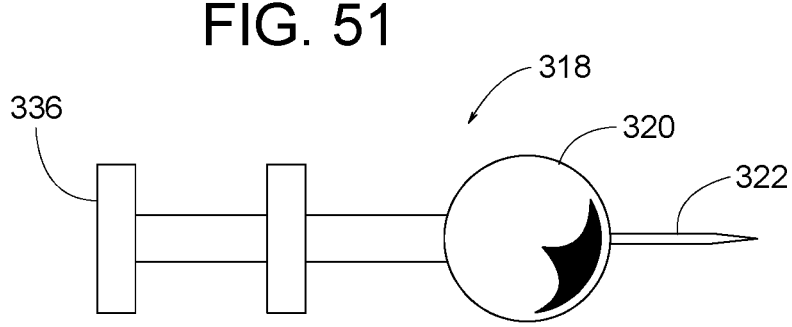
FIG. 51 is a side view of an example analog with a protruding pin.
Figure 52:
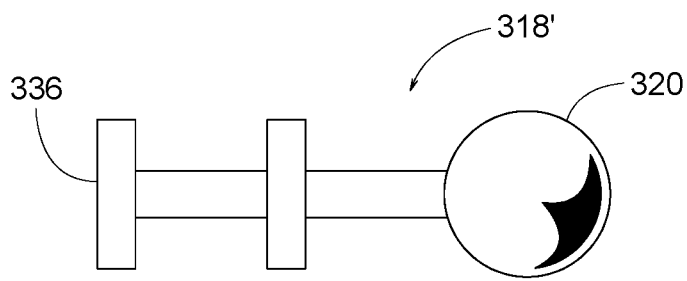
FIG. 52 is a side view of the analog shown in FIG. 51 but with its pin removed.

FIG. 51 shows what's known as an analog 318. In some examples, analog 318 is basically a combination of anchor 276 and marker body 36 (or actually a marker body model 320 of the same size and shape of marker body 36). Some examples of analog 318 include a pin 322, which will be explained later with reference to FIGS. 64-69. In some examples, pin 322 can be broken off, cut off, ground off, or otherwise removed from marker body model 320 to create an analog 318', as shown in FIG. 52.

Figure 53:
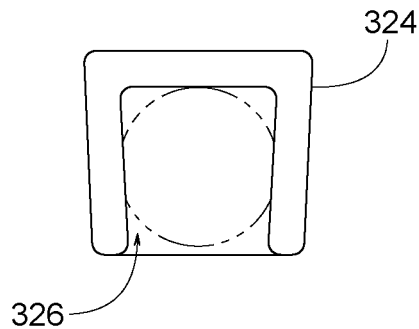
FIG. 53 is atop view of FIG. 54
Figure 54:
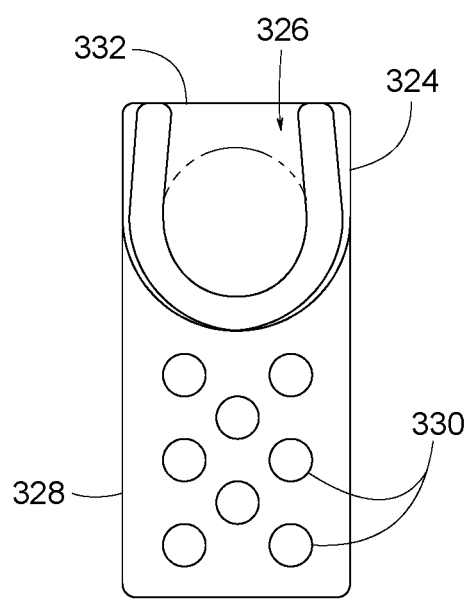
FIG. 54 is a front view of an example holder.
Figure 55:
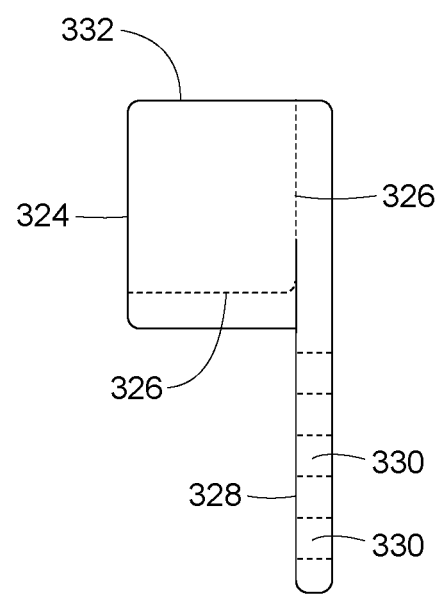
FIG. 55 is a right side view of FIG. 54.
Figure 56:
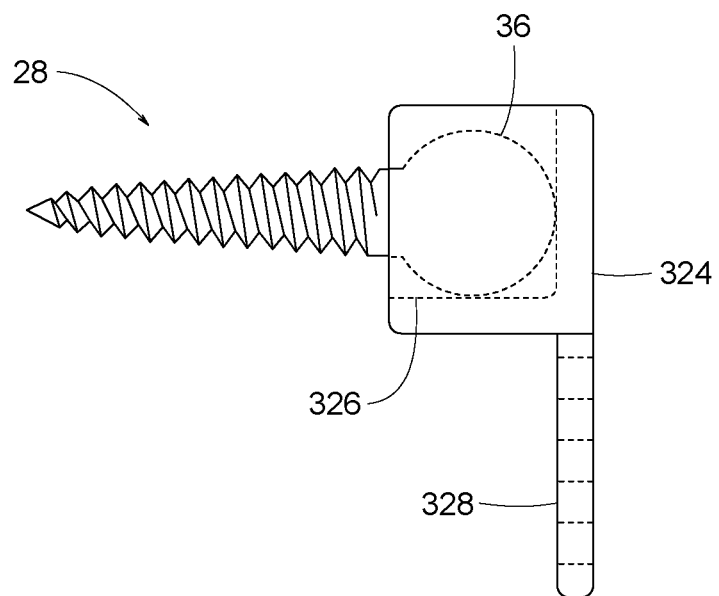
FIG. 56 is a right side view similar to FIG. 55 but with the example fiducial marker of FIG. 49 inserted in the holder.
Figure 57:
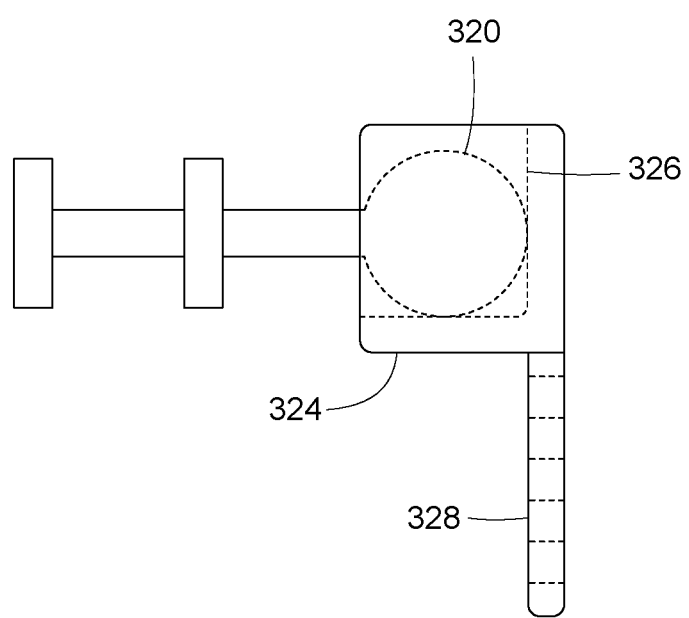
FIG. 57 is a right side view similar to FIG. 55 but with the example analog of FIG. 52 inserted in the holder.

FIGS. 53-55 show an example holder 324, which is somewhat of a substitute for holder 260 of FIGS. 38-43. Holder 324 includes a receptacle 326 for receiving selectively marker body 36 or marker body model 320. Holder 324 is of a size and shape to create a snap-in or interference fit with marker body 36 (FIG. 56) and marker body model 320 (FIG. 57). Some examples of holder 324 include an appendage 328 that helps secure holder 324 in position, as will be explained later with reference to FIGS. 58-63.

Figure 58:
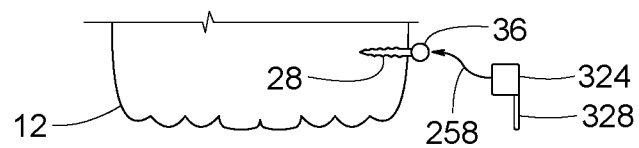
FIG. 58 is a schematic diagram illustrating another method step for analyzing jaws of a patient.

FIGS. 58-63 illustrate an alternative to the example shown in FIGS. 38-43, wherein FIGS. 58-63 correspond to FIGS. 38-43, respectively. FIG. 58 shows fiducial marker 28 screwed into jaw 12. Arrow 258 represents attaching holder 324 to marker body 36.

Figure 59:
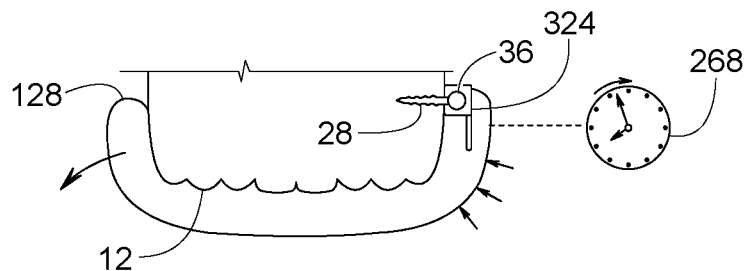
FIG. 59 is a schematic diagram illustrating another method step for analyzing jaws of a patient.

FIG. 59 shows holder 324 snapped onto or otherwise firmly attached to marker body 36 while molding material 128 encases holder 324 and much of jaw 12. The holder's appendage 328 is of a shape that securely anchors holder 324 to the set molding material 128. In some examples, appendage 328 includes multiple holes 330 to enhance the bond between appendage 328 and molding material 128. Holder 324 is particularly useful in cases where fiducial marker 28 is beyond a reasonable reach of molding material 128 within jaw 12.

Figure 60:
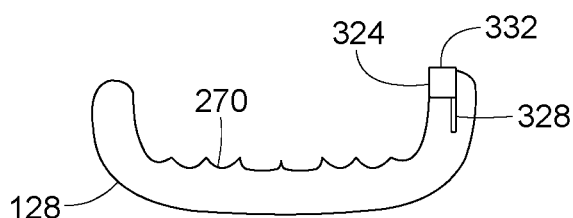
FIG. 60 is a schematic diagram illustrating another method step for analyzing jaws of a patient.

After molding material 128 sets, molding material 128 (impression) is removed from jaw 12 and separated from fiducial marker 28, while holder 324 remains encased within molding material 128, as shown in FIG. 60. Holder 324 has an open end 332 that allows marker body 36 to slide vertically out from within receptacle 326 as molding material 128 is removed from jaw 12.

Figure 61:
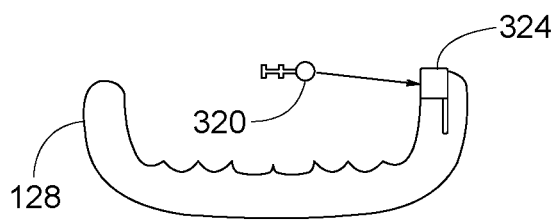
FIG. 61 is a schematic diagram illustrating another method step for analyzing jaws of a patient.

FIG. 61 shows marker body model 320 of analog 318' being inserted into receptacle 326 of holder 324. It should be noted, however, that in this example, pin 322 is first removed from marker body model 318, as pin 322 is not needed for this particular method. As mentioned earlier, in some examples, marker body model 320 snaps into receptacle 326 to help hold marker body model 320 in place as casting material 252 is poured into mold cavity 270.

Figure 62:
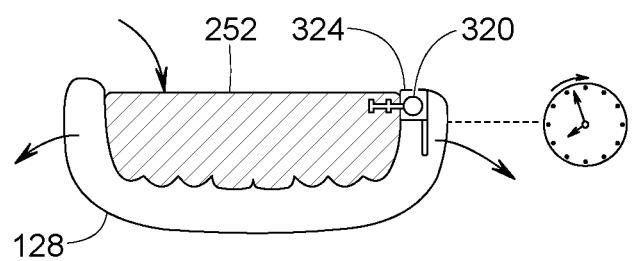
FIG. 62 is a schematic diagram illustrating another method step for analyzing jaws of a patient.
Figure 63:
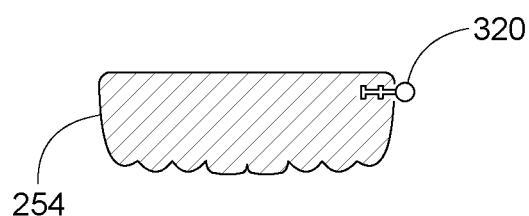
FIG. 63 is a schematic diagram illustrating another method step for analyzing jaws of a patient.

FIG. 62 shows casting material 252 having been poured into cavity 270, and thereby encasing one end 336 of analog 318'. After casting material 252 hardens to create cast model 254, molding material 128 is removed along with the embedded holder 324. FIG. 63 shows the resulting cast model 254 with the protruding marker body model 320. Marker body model 320 attached to cast model 254 can be used as a dimensional reference point, used as a tool attachment point, and/or used for carrying out various dental procedures.

Figure 64:
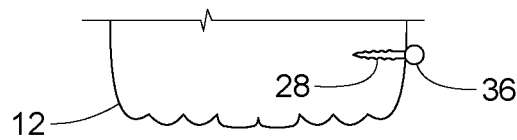
FIG. 64 is a schematic diagram illustrating another method step for analyzing jaws of a patient.

FIGS. 64-69 illustrate another alternative to the example shown in FIGS. 38-43, wherein FIGS. 64-69 correspond to FIGS. 38-43, respectively. The method shown in FIGS. 64-69 can be used when fiducial marker 28 is well within the reach of molding material 128. In this example, FIG. 64 shows fiducial marker 28 screwed into jaw 12.

Figure 65:
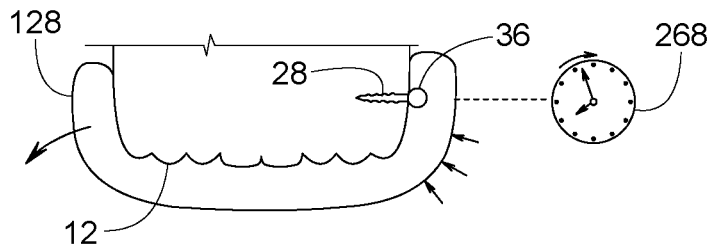
FIG. 65 is a schematic diagram illustrating another method step for analyzing jaws of a patient.
Figure 66:
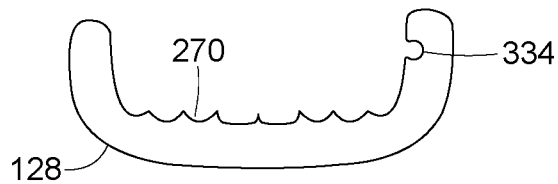
FIG. 66 is a schematic diagram illustrating another method step for analyzing jaws of a patient.

FIG. 65 shows molding material 128 encasing marker body 36 and a significant portion of jaw 12. After molding material 128 sets, molding material 128 is removed from jaw 12 and separated from fiducial marker 28, as shown in FIG. 66. The removal of marker body 36 from molding material 128 leaves a marker cavity 334 in the set molding material 128. Marker cavity 334 provides an accurate impression of marker body 36.

Figure 67:
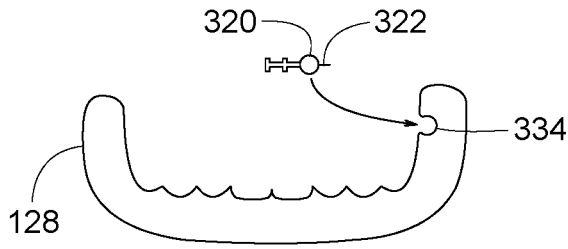
FIG. 67 is a schematic diagram illustrating another method step for analyzing jaws of a patient.

FIG. 67 shows marker body model 320 of analog 318 being inserted into marker cavity 334 of molding material 128. Upon pressing marker body model 320 into marker cavity 334, pin 322 pokes into molding body 128, which prevents marker body model 320 from rotating within marker cavity 334. Consequently, marker body model 320 is held firmly in place as casting material 252 is poured into mold cavity 270.

Figure 68:
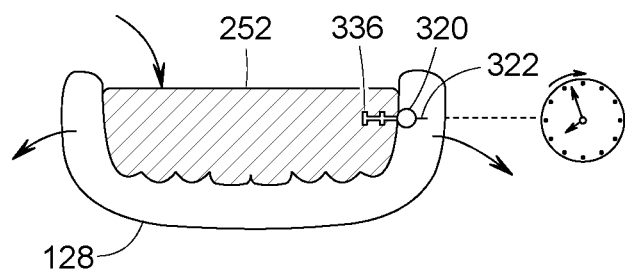
FIG. 68 is a schematic diagram illustrating another method step for analyzing jaws of a patient.
Figure 69:
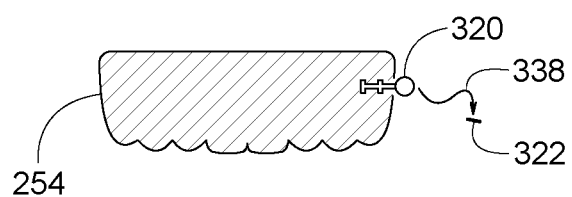
FIG. 69 is a schematic diagram illustrating another method step for analyzing jaws of a patient.
Figure 70:
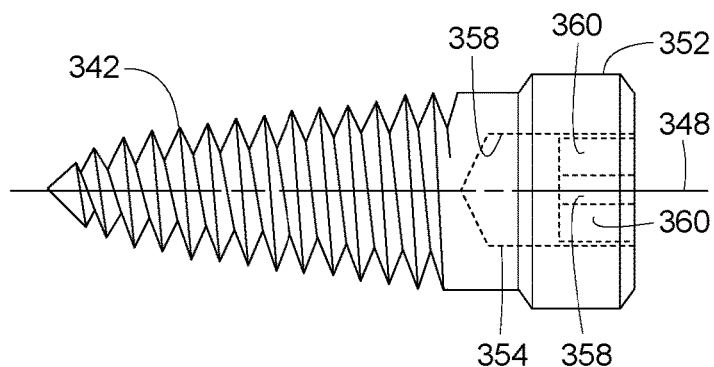
FIG. 70 is a side view similar to FIG. 45 but showing another example screw constructed in accordance with the teachings disclosed herein.
Figure 71:
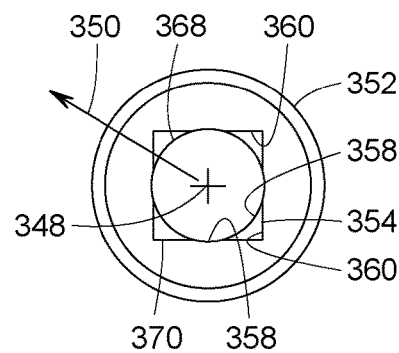
FIG. 71 is a right end view of FIG. 70.

FIG. 68 shows casting material 252 having been poured into mold cavity 270, and thereby encasing one end 336 of analog 318. After casting material 252 hardens to create cast model 254, molding material 128 is removed from cast model 254 and from analog 318 embedded therein. FIG. 69 shows the resulting cast model 254 with the protruding marker body model 320 with its pin 322. Arrow 338 represent removing pin 322 from marker body model 320, as pin 322 has served its purpose and is no longer needed. Marker body model 320 attached to cast model 254 can now be used as a dimensional reference point, used as a tool attachment point, and/or used for carrying out various dental procedures.

Figure 72:
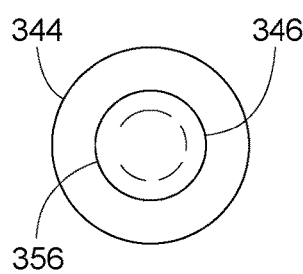
FIG. 72 is a left end view of FIG. 73.
Figure 73:
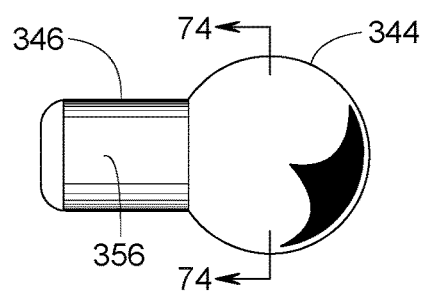
FIG. 73 is a side view similar to FIG. 45 but showing another example marker body and extension constructed in accordance with the teachings disclosed herein.
Figure 74:
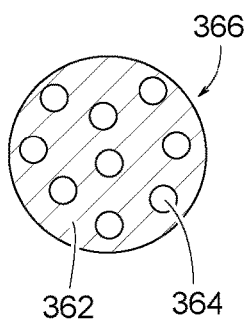
FIG. 74 is a cross-sectional view taken along line 74-74 of FIG. 73.
Figure 75:
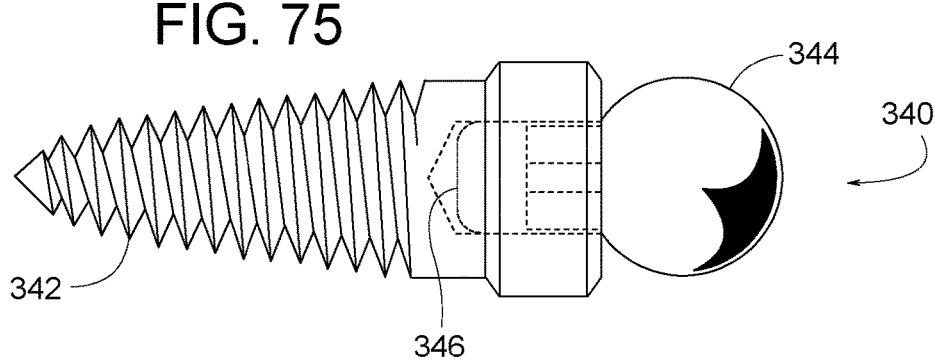
FIG. 75 is a side view similar to FIG. 48 but showing the example screw and marker body of FIGS. 70-74.
Figure 76:
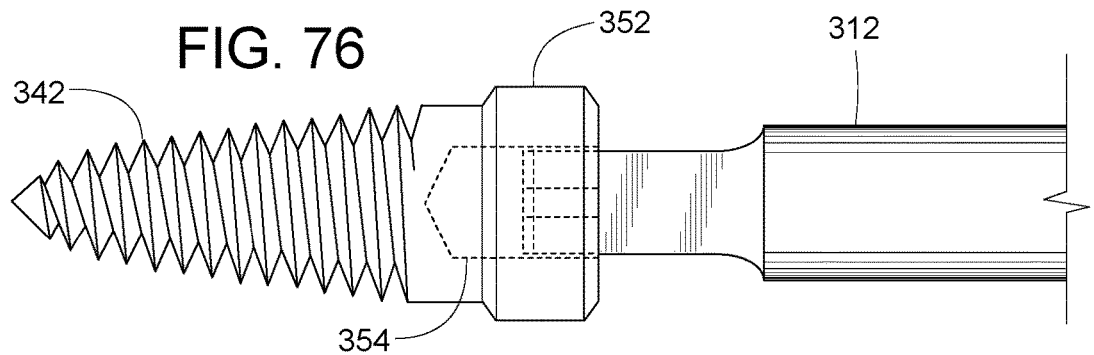
FIG. 76 is a side view similar to FIG. 47 but showing the example screw of FIGS. 70 and 71 and the example tool of FIGS. 45 and 47.

FIGS. 70-76 show an example fiducial marker 340 similar to the example shown in FIGS. 45-48 but with some improvements. Fiducial marker 340, in this example, includes a screw 342 (FIGS. 70 and 71) and a marker body 344 with an extension 346 (FIGS. 72, 73 and 74).

Screw 342 is elongate to define a longitudinal axis 348 that is perpendicular to a radial direction 350. A head 352 of screw 342 defines a socket 354 for receiving selectively extension 346 of marker body 344 or tool 312. In some examples, extension 346 has a substantially cylindrical outer surface 356, so extension 346 can be easily inserted into socket 354 in any rotational orientation. The term, "head" simply refers to one end of screw 342 and does not necessarily mean that head 342 is of a larger diameter than the rest of screw 342. In some examples, screw 342 and head 352 provide a monolithic piece of a first material consisting mostly of a metal (e.g., titanium, tungsten, stainless steel, etc.).

In the illustrated example, socket 354 includes a cylindrical inner surface 358 and a plurality of inward facing facets 360. Cylindrical inner surface 358 is substantially concentric with longitudinal axis 348. Facets 360 are substantially parallel to the screw's longitudinal axis 348. The term, "inward facing facets" means that the facets 360 face into the central cavity of socket 354.

To reduce radiographic scatter and image distortion, marker body 344 is made of a second material that is less radiopaque than the first material of screw 342. So, in some examples, the second material is a mixture 366 of a polymeric binder 362 and a radiopaque filler material 364. In some examples, extension 346 is a seamless integral extension of marker body 344, whereby marker body 344 and extension 346 are both made of the second material.

Some examples of polymeric binder 362 include acrylic, polymethyl methacrylate (PMMA), polycarbonate, polystyrene, high-impact polystyrene (HIPS). Some examples of filler material 364 include metallic material, barium, titanium, bismuth, tungsten, zirconium, and various compounds thereof. In some examples, filler material 364 includes barium sulfate, which can be finely mixed with polymeric binder 362.

In some examples, the proportions of binder 362 and filler material 364 may be important. Too much filler material 364 may create one or more problems, such as undesirable scatter in first scan result 98, structural weakness in extension 346, and/or difficulty in plastic injection molding the material. An insufficient amount of filler material 364 may render marker body 344 so radiographically transparent that it becomes difficult to distinguish marker body 344 from human tissue. Consequently, in some examples, filler material 364 is more than twice as dense as polymeric binder 362 and makes up 20% to 70% of the mixture's volume to provide mixture 366 with a density of 1.8 to 2.9 grams per cubic centimeter, which falls somewhere between the density of jaw bone and tooth enamel. Particularly favorable results are achieved when mixture 366 is mostly polymeric binder 362 by volume (i.e., polymeric binder 362 contributes at 50% of the mixture's volume).

Socket 354 is of a size and shape to receive selectively tool 312 or the marker body's extension 346. Fiducial maker 340 provides a press-fit in radial direction 350 between the substantially cylindrical outer surface 356 of extension 346 and the substantially cylindrical inner surface 358 of socket 354 when extension 346 is inserted into socket 354. Tool 312 engages the plurality of inward facing facets 360 when tool 312 is inserted into socket 354. Fiducial marker 340 provides a slip-fit in radial direction 350 between tool 312 and socket 354 when tool 312 is inserted into socket 354.

The term, "press-fit" refers to two parts fitting matingly together by virtue of at least one of the parts being in compression or tension rather than relying on clearance between the parts. The term, "slip-fit" refers to two parts fitting matingly together by virtue of clearance between the parts rather than relying on compression or tension of one or both of the parts.

To provide socket 354 with both cylindrical surface 358 and inward facing facets 360, some examples of screw 342 include both a round hole 368 (cylindrical hole) and a square hole 370, which are concentric with each other. In some examples, round hole 368 serves as a drilled pilot hole for facilitating the subsequent broaching of square hole 370.

Here are some additional points worth noting. The term, "computer" refers to computer hardware itself plus software programs running thereby either locally or remotely. The term, "substantially match" refers to a comparison with differences that have been minimized. The terms, "first perspective" and "second perspective" refer to directions in which a virtual 3D object is viewed. For example, a first perspective could be a front view along a Z-axis, and a second perspective could be a side view along an X-axis. A top view along a Y-axis is another example perspective. First and second perspectives do not necessarily have to be perpendicular to each other.

Although certain example methods, apparatus and articles of manufacture have been disclosed herein, the scope of coverage of this patent is not limited thereto. On the contrary, this patent covers all methods, apparatus and articles of manufacture fairly falling within the scope of the claims of this patent.

The invention claimed is:

1. A fiducial marker adapted to be screwed into a jawbone via a tool, the fiducial marker comprising:
   a screw being elongate to define a longitudinal axis that is perpendicular to a radial direction;
   a head on the screw, the head defining a socket, the screw and the head being of a monolithic piece of a first material that is radiopaque, the first material consisting mostly of a metal;
   a marker body being formed of a mixed material, wherein components of the mixed material include a polymeric binder and a filler material, the proportion of the components being the same throughout any given sample of the mixed material, the filler material being 20% to 70% by volume of the mixed material, the filler material being more than twice as dense as the polymeric binder, the mixed material having a density of 1.8 to 2.9 grams per cubic centimeter, the mixed material of the marker body being less radiopaque than the first material of the screw; and
   an extension extending from the marker body, the socket being of a size and shape to receive selectively the tool and the extension, the tool matingly engaging the socket when the tool is disposed within the socket.

2. The fiducial marker of claim 1, wherein the extension includes a cylindrical outer surface, the socket includes a cylindrical inner surface that is concentric with the longitudinal axis of the screw, and the socket includes a plurality of inward facing facets that are parallel to the longitudinal axis of the screw.

3. The fiducial marker of claim 2, wherein the fiducial maker provides a press-fit in the radial direction between the cylindrical outer surface and the cylindrical inner surface when the extension is disposed within the socket, the tool engages the plurality of inward facing facets when the tool is disposed within the socket, and the fiducial marker provides a slip-fit in the radial direction between the tool and the socket when the tool is disposed within the socket.

4. The fiducial marker of claim 1, wherein the filler material is metallic.

5. The fiducial marker of claim 1, wherein the filler material includes barium sulfate.

6. The fiducial marker of claim 1, wherein the extension is a seamless integral extension of the marker body, whereby both the marker body and the extension are of the mixed material.

7. A fiducial marker adapted to be screwed into a jawbone via a tool, the fiducial marker comprising:
   a screw being elongate to define a longitudinal axis that is perpendicular to a radial direction;
   a head on the screw, the head defining a socket, the screw and the head being of a monolithic piece of a first material that is radiopaque, the first material consisting mostly of a metal;
   a cylindrical inner surface within the socket, the cylindrical inner surface being concentric with the longitudinal axis of the screw;
   a plurality of inward facing facets on the head to define at least some of the socket, the plurality of inward facing facets being parallel to the longitudinal axis of the screw;
   a marker body being formed of a mixed material, wherein components of the mixed material include a polymeric binder and a filler material, the proportion of the components being the same throughout any given sample of the mixed material, the filler material being 20% to 70% by volume of the mixed material, the filler material being more than twice as dense as the polymeric binder, the mixed material having a density of 1.8 to 2.9 grams per cubic centimeter, the mixed material of the marker body being less radiopaque than the first material of the screw;
   an extension extending from the marker body; and
   a cylindrical outer surface on the extension, the socket being of a size and shape to receive selectively the tool and the extension, the fiducial maker providing a press-fit in the radial direction between the cylindrical outer surface and the cylindrical inner surface when the extension is disposed within the socket, the tool engaging the plurality of inward facing facets when the tool is disposed within the socket, and the fiducial marker providing a slip-fit in the radial direction between the tool and the socket when the tool is disposed within the socket.

8. The fiducial marker of claim 7, wherein the filler material is metallic.

9. The fiducial marker of claim 7, wherein the filler material includes barium sulfate.

10. The fiducial marker of claim 7, wherein the extension is a seamless integral extension of the marker body, whereby both the marker body and the extension are of the mixed material.

* * * * *